US008883729B2

(12) United States Patent
Hoeprich et al.

(10) Patent No.: US 8,883,729 B2
(45) **Date of Patent: *Nov. 11, 2014**

(54) NANOLIPOPROTEIN PARTICLES AND RELATED COMPOSITIONS, METHODS AND SYSTEMS

(75) Inventors: Paul D. Hoeprich, Pleasanton, CA (US); Nicholas O. Fischer, Livermore, CA (US); Peter W. Mason, Somerville, MA (US); Craig D. Blanchette, Moraga, CA (US)

(73) Assignees: Lawrence Livermore National Security, LLC, Livermore, CA (US); The Board of Regents of the University of Texas System, Austin, TX (US)

( * ) Notice: Subject to any disclaimer, the term of this patent is extended or adjusted under 35 U.S.C. 154(b) by 911 days.

This patent is subject to a terminal disclaimer.

(21) Appl. No.: 12/469,533

(22) Filed: May 20, 2009

(65) Prior Publication Data

US 2009/0311276 A1 Dec. 17, 2009

Related U.S. Application Data

(60) Provisional application No. 61/055,380, filed on May 22, 2008.

(51) Int. Cl.
*C07K 14/00* (2006.01)
*A61K 47/48* (2006.01)

(52) U.S. Cl.
CPC ....... *A61K 47/48853* (2013.01); *A61K 47/4833* (2013.01); *Y10S 977/799* (2013.01)
USPC .............................. 514/12; 530/350; 977/799

(58) Field of Classification Search
None
See application file for complete search history.

(56) References Cited

U.S. PATENT DOCUMENTS

| | | | |
|---|---|---|---|
| 4,317,771 | A | 3/1982 | Shiba et al. |
| 5,393,530 | A | 2/1995 | Schneider et al. |
| 7,048,949 | B2 | 5/2006 | Sligar et al. |
| 7,083,958 | B2 | 8/2006 | Sligar et al. |
| 7,375,234 | B2 | 5/2008 | Sharpless et al. |
| 2005/0182243 | A1 | 8/2005 | Sligar et al. |
| 2006/0189554 | A1 | 8/2006 | Mumper et al. |
| 2006/0211092 | A1 | 9/2006 | Sligar et al. |
| 2007/0117179 | A1 | 5/2007 | Kudlicki et al. |
| 2008/0124350 | A1 | 5/2008 | Mumper et al. |
| 2009/0136937 | A1 | 5/2009 | Coleman et al. |
| 2009/0311276 | A1 | 12/2009 | Hoeprich et al. |
| 2011/0059549 | A1 | 3/2011 | Coleman et al. |
| 2011/0195450 | A1 | 8/2011 | Kudlicki et al. |

FOREIGN PATENT DOCUMENTS

| | | |
|---|---|---|
| WO | 02/40501 | 5/2002 |
| WO | 2004/094651 | 11/2004 |
| WO | 2005/070400 | 8/2005 |
| WO | 2006/073419 | 7/2006 |
| WO | 2007/053655 | 5/2007 |
| WO | 2008/106660 | 9/2008 |

OTHER PUBLICATIONS

Schmitt et al.,"Synthesis and Characterization of chelator-lipids for reversible immobilization of engineered proteins at self-assembled lipid interfaces", J. Am. Chem. Soc. 116: 8485-8491 (1994).*

Petrakova, O., Volkova, E., Gorchako, R., Paessler, S., Kinney, R.M., and Frolov, I., Noncytopathic replication of Venezuelan equine encephalitis virus and eastern equine encephalitis virus replicons in Mammalian cells. J Virol 79, 7597-608 (2005).

Konishi, E., and Mason, P.W., Proper maturation of the Japanese encephalitis virus envelope glycoprotein requires co-synthesis with the premembrane protein. J Virol 67, 1672-5 (1993).

Widman, D. G., Ishikawa, T., Fayzulin, R., Bourne, N., Mason, P.W., Construction and characterization of a second-generation pseudoinfectious West Nile virus vaccine propagated using a new cultivation system. Vaccine 26, 2762-71 (2008).

Chromy, B.A., et al., Different Apolipoproteins Impact Nanolipoprotein Particle Formation. J. Amer. Chem. Soc. 129, 14348-54 (2007).

Fischer, N., et al., Immobilization of His-Tagged Proteins on Nickel-Chelating Nanolipoprotein Particles. Bioconjugate Chemistry 20, 460-5 (2009).

Terpe, K., Overview of tag protein fusions: from molecular and biochemical fundamentals to commercial systems. Appl Microbiol Biotechnol, 60, 523-33 (2003).

Kolb, H. and Sharpless, B., The growing impact of click chemistry on drug discovery. Drug Discov. Today, 8, 1128-37 (2003).

Simon, S.R. and Konigsberg, W.H., Chemical modification of hemoglobins: a study of conformation restraint by internal bridging. Proc. N.A.S. USA, 56, 749-56 (1966).

Martin, B.R. and Cravatt, B.F., Large-scale profiling of protein palmitoylation in mammalian cells. Nat. Methods 6, 135-38 (2009).

Blanchette, C.D., Quantifying size distributions of nanolipoprotein particles with single-particle analysis and molecular dynamic simulations. J Lipid Res. 49, 1420-30 (2008).

Patel, J.D., et al., Preparation and Characterization of Nickel Nanoparticles for Binding to His-tag Proteins and Antigens. Pharmaceutical Research, vol. 24, No. 2 (2006).

PCT International Search Report issued for PCT Application No. PCT/US2009/044722 filed May 20, 2009, in the name of Lawrence Livermore National Security, LLC.

PCT Written Opinion issued for PCT Application No. PCT/US2009/044722 filed May 20, 2009, in the name of Lawrence Livermore National Security, LLC.

Hein, C.D., et al., Click Chemistry, A Powerful Tool for Pharmaceutical Sciences. Pharmaceutical Research 2008, vol. 25, No. 10:2216-2230.

Dalpke, A.H., et al., Phosphodiester CpG oligonucleotides as adjuvants: polyguanosine runs enhance cellular uptake and improve immunostimulative activity of phosphodiester CpG oligonucleotides in vitro and in vivo, Immunology 2002, 106:102-112.

(Continued)

*Primary Examiner* — Anand Desai
(74) *Attorney, Agent, or Firm* — Steinfl & Bruno, LLP

(57) ABSTRACT

Functionalized nanolipoprotein particle presenting an anchor substrate compound for binding with a corresponding anchor compound presented on a target molecule, and related compositions methods and systems.

35 Claims, 7 Drawing Sheets

(56) References Cited

OTHER PUBLICATIONS

Weermata, R.D., et al., CpG DNA induces stronger immune responses with less toxicity than other adjuvants. Vaccine 2000, 18:1755-62.

Ueda, H., et al., Induction of tumor necrosis factor-a in solid tumor region by the orally administered synthetic muramyl dipeptide analogue, romurtide, Int'l Immunopharm. 2001, 1:97-104.

Osada, Y., et al., Polymorphonuclear Leukocyte Activation by a Synthetic Muramyl Dipeptide Analog, Inf. Immun. 1982, 38:848-854.

Huleatt, J.W., et al., Potent immunogenicity and efficacy of a universal influenza vaccine candidate comprising a recombinant fusion protein linking influenza M2e to the TLR5 ligand flagellin. Vaccine 2007, 26:201-214.

Hamdy, S., et al., Pharmaceutical analysis of synthetic lipid A—based vaccine adjuvants in poly (d,l-lactic-co-glycolic acid) nanoparticle formulations. Journal of Pharmaceutical and Biomedical Analysis, 2007, 44:914-923.

Giannini, S.L, et al., Enhanced humoral and memory B cellular immunity using HPV16/18 L1 VLP vaccine formulated with the MPL/aluminium salt combination (AS04) compared to aluminium salt only. Vaccine, 2006, 24:5937-5949.

Fitzgerald, K.A., et al., The Shape of Things to Come. Science, 2007, 316:1574-1576.

Author Unknown, Special Report, Dengue fever climbs the social ladder, Nature 2007, 448: 734-735.

Bayburt, T. H., et al., Self-Assembly of Discoidal Phospholipid Bilayer Nanoparticles with Membrane Scaffold Proteins, Nano Lett. 2002, 2: 853-856.

Bijsterbosch, M., et al., Specific targeting of a lipophilic prodrug of iododeoxyuridine to parenchymal liver cells using lactosylated reconstituted high density lipoprotein particles, Biochemical Pharmacology 1996, 52: 113-121.

Jasanada, F., et al., Indium-111 labeling of low density lipoproteins with the DTPA-Bis(stearylamide): Evaluation as a potential radiopharmaceutical for tumor localization, Bioconjugate Chemistry 1996, 7: 72-81.

Masquelier, M., et al., Low-density lipoprotein as a carrier of antitumoral drugs: In Vivo fate of drug-human low-density lipoprotein complexes in mice, Cancer Research 1986, 46: 3842-3847.

Rensen, P., et al., Recombinant lipoproteins: lipoprotein-like lipid particles for drug targeting, Advanced Drug Delivery Reviews 2001, 47: 251-276.

Gupta, R., et al., Adjuvants for human vaccines—current status, problems and future prospects, Vaccine 1995, 13: 1263-1276.

Okemoto, K., et al., A Potent Adjuvant Monophosphoryl Lipid A Triggers Various Immune Responses, but Not Secretion of IL-1β or Activation of Caspase-1, The Journal of Immunology 2006, 176: 1203-1208.

Mata-Haro, V., et al., The vaccine adjuvant monophosphoryl lipid A as a TRIF-biased agonist of TLR4, Science 2007, 316: 1628-1632.

Persing, D., et al., Taking toll: lipid A mimetics as adjuvants and immunomodulators, Trends in Microbiology 2002, 10: S32-S37.

Zimmermann, et al., Immunostimulatory DNA as adjuvant: efficacy of phosphodiester CpG oligonucleotides is enhanced by 3' sequence modifications (2003) Vaccine 21:990-995.

Chaung, et al., CpG oligodeoxynucleotides as DNA adjuvants in vertebrates and their applications in immunotherapy (2006) Int'l Immunopharm. 6:1586-1596.

Ruger, et al., In vitro characterization of binding and stability of single-chain Fv Ni-NTA-liposomes, (2006) J. Drug Targeting 14:576-582.

Ruger, et al., Generation of immunoliposomes using recombinant single-chain Fv fragments bound to Ni-NTA-liposomes (2005) J. Drug Targeting 13:399-406.

Chikh, et al., Attaching histidine-tagged peptides & proteins to lipid-based carriers through use of metal-ion-chelating lipids (2002) BBA 1567:204-212.

Ulmer, et al.,Vaccine manufacturing: challenges and solutions (2006) Nature Biotech. 24:1377-1383.

Katzen, F., et al., Insertion of Membrane Proteins into Discoidal Membranes using a Cell-free Protein Expression Approach, J. Proteome Res., 2008, vol. 7, pp. 3535-3542.

Cappuccio, et al., Cell-free Co-expression of Functional Membrane Proteins and Apolipoproteins Forming Soluble Nanolipoprotein Particles, (2008) Molecular & Cellular Proteomics 7.11:2246-2253.

Blanchette, C.D., et al., Characterization and Purification of Polydisperse Reconstituted Lipoproteins and Nanolipoprotein Particles. International Journal of Molecular Sciences 2009, 10:2958-2971.

Blanchette, C.D., et al., Atomic force microscopy differentiates discrete size distributions between membrane protein containing and empty nanolipoprotein particles, Biochimica et Biophysica Acta 1788, 2009, pp. 724-731.

Fischer, N.O., et al., Conjugation to Nickel-Chelating Nanolipoprotein Particles Increases the Potency and Efficacy of Subunit Vaccines to Prevent West Nile Encephalitis, Bioconjugate Chem., 2010, vol. 21, pp. 1018-1022.

Restriction Requirement issued for U.S. Appl. No. 12/604,362, filed Oct. 22, 2009, in the name of Paul D. Hoeprich et al.; mail date Jan. 11, 2012.

Ratanabanangkoon, P. et al., Two-Dimensional Streptavidin Crystals on Giant Lipid Bilayer Vesicles, Langmuir 2002, vol. 18, pp. 4270-4276.

Bischler, N. et al, Specific Interaction and Two-Dimensional Crystallization of Histidine Tagged Yeast RNA Polymerase I on Nickel-Chelating Lipids, Biophysical Journal, Mar. 1998, vol. 74, pp. 1522-1532.

Kubalek, E.W. et al., Two-Dimensional Crystallization of Histidine-Tagged, HIV-1 Reverse Transcriptase Promoted by a Novel Nickel-Chelating Lipid, Journal of Structural Biology, 1994, vol. 113, pp. 117-123.

Lasic et al. "Novel Applications of Liposomes" *Trends Biotechnol.* 1998, 16, 307-321.

Boroske et al. "Osmotic Shrinkage of Giant Egg-Lecithin Vesicles" *Biophys. J.* 1981, 34, 95-109.

Disalvo et al. "Surface changes induced by osmotic shrinkage on large unilamellar vesicles" *Chem. Phys. Lipids* 1996, 84, 35-45.

Choquet et al. "Stability of pressure-extruded liposomes made from archaeobacterial ether lipids" *Appl. Microbiol. Biotechnol.* 1994, 42, 375-384.

Liang et al. "Mechanical properties and stability measurement of cholesterol-containing liposome on mica by atomic force microscopy" *J. Colloid Interface Sci.* 2004, 278, 53-62.

Hernández-Caselles et al. "Influence of liposome charge and composition on their interaction with human blood serum proteins" *Mol. Cell. Biochem.* 1993, 120, 119-126.

Restriction Requirement mailed on Jan. 11, 2012 for U.S. Appl. No. 12/604,362, filed Oct. 22, 2009 in the name of Paul D. Hoeprich et al.

Non-Final Office Action mailed on May 7, 2012 for U.S. Appl. No. 12/604,362, filed Oct. 22, 2009 in the name of Paul D. Hoeprich et al.

Stryer "Lipid Vesicles (Liposomes) and Planar Membranes Are Valuable Model Systems" *Biochemistry*, 4th Ed. W.H. Freeman and Company, New York: 1995, p. 271.

Kostarelos et al. "Steric stabilization of phospholipid vesicles by block copolymers: Vesicle Flocculation and osmotic swelling caused by monovalent and divalent cations" *J. Chem. Soc., Faraday Trans.*, 1998, 94, 2159-2168.

Final Office Action mailed on Jan. 18, 2012 for U.S. Appl. No. 12/118,396, filed May 9, 2008 in the name of Matthew A. Coleman et l.

Barros, F., et al., Modulation of human erg K+ channel gating by activation of a G protein-coupled receptor and protein kinase C, J. Physiology 1998, 511: 333-346.

Dong, F., et al., Endothelin-1 enhances oxidative stress, cell proliferation and reduces apoptosis in human umbilical vein endothelial cells: role of ETB receptor, NADPH oxidase and caveolin-1 British J. of Pharmacology 2005, 145: 323-333.

Dumartin, B., et al., Dopamine tone regulates D1 receptor trafficking and delivery in striatal neurons in dopamine transporter-deficient mice, PNAS 2000, 97: 1879-1884.

Gantz, I., et al.,Molecular cloning of a gene encoding the histamine H2 receptor, PNAS 1991, 88: 429-433.

(56) References Cited

OTHER PUBLICATIONS

Hauger, R., et al., Corticotropin Releasing Factor (CRF) Receptor Signaling in the Central Nervous System: New Molecular Targets, CNS Neurol. Discord. Drug Target 2006, 5: 453-479.
Hong, Y., et al., G-Protein-Coupled Receptor Microarrays for Multiplexed Compound ScreeningJ. Biomol. Screening 2006, 11: 435-438.
Metz, J., et al ACTH, a-MSH, and control of cortisol release: cloning, sequencing, and functional expression of the melanocortin-2 and melanocortin-5 receptor in *Cyprinus carpio*Am. J. Physiol. Regul. Integr. Comp. Physiol. 2005, 289: R814-R826.
Pettibone, D., et al., The Effects of Deleting the Mouse Neurotensin Receptor NTR1 on Central and Peripheral Responses to NeurotensinJ. Pharma. & Exp. Therapeutics 2002, 300: 305-313.
Ren, X., et al., Different G protein-coupled receptor kinases govern G protein and b-arrestin-mediated signaling of V2 vasopressin receptor, PNAS 2005, 102: 1448-1453.
Adrenergic Receptor, Wikipedia 2006, http://web.archive.org/web/20061230132111/http://en.wikipedia.org/wiki/Adrenergic__Receptor.
5-HT Receptor, Wikipedia 2007, http://web.archive.org/web/20071109235348/http://en.wikipedia.org/wiki/5-HT__receptor.
Muscarinic Acetylcholine Receptor, Wikipedia 2007, http://web.archive.org/web/20071020193657/http://en.wikipedia.org/wiki/Muscarinic__acetylcholine__receptor.
G Protein-coupled Receptor, Wikipedia 2008, http://web.archive.org/web/20080224232212/http://en.wikipedia.org/wiki/G__protein-coupled__receptor.
Advisory Action mailed on Jun. 6, 2012 for U.S. Appl. No. 12/118,530, filed May 9, 2008 in the name of Matthew A. Coleman et al.
Final Office Action mailed on Jun. 7, 2012 for U.S. Appl. No. 12/352,472, filed Jan. 12, 2009 in the name of Sarah E. Baker et al.
Non-Final Office Action issued for U.S. Appl. No. 12/352,548, filed Jan. 12, 2009 in the name of Brett A. Chromy et al., mail date: Sep. 13, 2011.
Notice of Allowance issued for U.S. Appl. No. 12/352,548, filed Jan. 12, 2009 in the name of Brett A. Chromy, mail date: Mar. 12, 2012.
Chefson, A. et al., Progress towards the easier use of P450 enzymes, Mol. bioSyst., 2006, 2, 462-469.
Lubert Stryer et al., Oxygen Binds to a Heme Prosthetic Group, Biochemistry 1995, 4th edition, 148.
Wuu, J. et al., High yield cell-free production of integral membrane proteins without refolding or detergents, BBA 2008, 1778:1237-1250.
Final Office Action for U.S. Appl. No. 12/118,396, filed May 5, 2008 in the name of Matthew A. Coleman et al., mail date: Jan. 18, 2012.
Cullis P.R., et al., Physical Properties and Functional Roles of Lipids in membranes, Biochemistry of Lipids, Lipoproteins and Membranes, 1991, Chapter 1, pp. 1-41.
Silvius, J.R. Thermotropic Phase Transitions of Pure Lipids in Model Membranes and their Modification by Membrane Proteins, Lipid-Protein Interactions, 1982, vol. 2 pp. 239-281.
Non-Final Office Action issued for U.S. Appl. No. 12/118,396, filed May 9, 2008 in the name of Matthew A. Coleman et al.; mail date: Aug. 30, 2011.
Civjan, N.R. et al. Direct solubilization of heterologously expressed membrane proteins by incorporation into nanoscale lipid bilayers, Bio Techniques, 2003, 35(3), pp. 556-559 and 562-563.
Persson, B. et al. Topology prediction of membrane proteins, Protein Science, 1996, vol. 5, pp. 363-371.
Non-Final Office Action mailed on Sep. 22, 2011, 2011 U.S Appl. No. 12/352,472, filed Jan. 12, 2009 in the name of Sarah E. Baker et al.
Restriction Requirement issued for U.S. Appl. No. 12/352,548, filed Jan. 12, 2009 in the name of Brett A. Chromy et al.; mail date: Apr. 25, 2011.
Restriction Requirement issued for U.S. Appl. No. 12/352,472, filed Jan. 12, 2009 in the name of Sarah E. Baker et al.; mail date: May 27, 2011.
Restriction Requirement issued for U.S. Appl. No. 12/118,396, filed May 9, 2008 in the name of Matthew Coleman et al.; mail date: Mar. 4, 2011.
Sapra, R., et al., A simple energy-conserving system: Proton reduction coupled to proton translocation, PNAS 2003, 100: 7545-7550.
Zhang, Y.-H. P.; Evans, B. R.; Mielenz, J. R.; Hopkins, R. C.; Adams, M. W. W. "High-Yield Hydrogen Production from Startch and Water by a Synthetic Enzymatic Pathway", PLoS ONE 2007, e456, (S), 1-6. May 2007.
Sanderson, K., "The photon trap", Nature 2008, 452, 400-402.
Woodward, J.; Mattingly, S. M.; Danson, M.; Hough, D.; Ward, N.; Adams, M. "In vitro hydrogen production by glucose dehydrogenase and hydrogenase", Nature Biotechnology 1996, 14,872-874.
Woodward, J.; Orr, M.; Cordray, K.; Greenbaum, E., "Enzymatic production of biohydrogen", Nature, 2000, 405, 1014-1015.
Elgren, T. E.; Zadvomy, O. A.; Brecht, E.; Douglas, T.; Zorin, N. A,; Maroney, M. J.; Peters, "Immobilization of Active Hydrogenases by Encapsulation in polymeric porous gels", Nano Letters 2005 vol. 5, No. 10 2085-2087.
Borch, J. et al., "Nanodiscs for immobilization of Lipid Bilayers and Membrane Receptors:", Analytical Chemistry 2008,80, (16), 6245-6252.
Nath, A,; Atkins, W. M.; Sligar, S. G. "Applications of Phospholipid . . . ", Biochemistry 2007,46, (8), 2059-2069.
Boldog, T.; Grimme, S.; Li, M.; Sligar, S.; Hazelbauer, G. L. "Nanodiscs separate chemoreceptor oligomeric states and reveal their signaling properties," Proceedings of the National Academy of Sciences 2006, 103, (31), I 1509-1 1514.
Leitz, A. J.; Bayburt, T. H.; Basnakov, A. N.; Springer, B. A,; Sligar, S. G., "Functional reconstitution of B2-adrenergic receptors utilizing self-assembling Nanodisc technology", Biotechniques 2006, 40, (5), 601-612.
Hedderich, R., "Energy-Converting [NiFi] Hydrogenases From Archaea and Extremophiles", Journal of Bioenergetics and Biomembranes 2004, 36, (1), 65-75.
Vignais PM. ; Billoud B. Ocurrence, Classification, and Biological Function of Hydrogenases: An overview. Chemical Reviews 2007, 107, 4206-4272.
Jed O. Eberly and Roger L. Ely, "Thermotolerant Hydrogenases", Critical Reviews in Microbiology, 34:117-130, 2008.
Sun, X. et al . Membrane-Mimetic Films of Aymmetric Phosphtidylcholine Lipid Bolaamphiphiles. Langmuir 2006,22, 1201-1208.
Meyer, J. "Fe/Fe hydrogenases and their evolution: a genomic perspective." Cell. Mol. Life. Sci. 64 2007 1063-1084.
Vincent, K. A. et al. "Investigating and Exploiting the Electrocatalytic Properties of Hydrogenases" Chern. Rev. 2007 107, 4366-4413.
Parkin, A., Goldet, G. Cavazza, C. Fontecilla-Camps, J., Armstrong, F. J., "The difference a Se Makes?", Am Chern. Soc. 2008,13 (40) 13410-13416.
North P. and Fleischer S. "Alteration of Synaptic Membrane Cholesterol/Phospholipid Ratio Using a Lipid Transfer Protein", (1983) J. Biol. Chem. vol. 258, No. 2. pp. 1242-1253.
Bockaert J., Brand C., Journot, L. (1997), Do Recombinant Receptor Assays Provide Affinity and Potency. In Receptor Classification: The integration of operational, structural, and transductional information (D.G. Trist, P.P.A. Humphrey, P. Leff, and N.P. Shankley, Eds.). vol. 812. New York, New York Academy of Sciences, pp. 55-70.
Tufteland M. et al., "Peptide Stabilized Amphotericin B nanodisks", Peptides (2007) 28:741-746.
Jonas, A. "Reconstitution of High-Density Lipoproteins", Methods Enzymol. 1986, 128, 553-582.
Bayburt, T. H.; Grinkova, Y. V.; Sligar, S. G."Self-Assembly of Discoidal Phospholipid Bilayer Nanoparticles with membrane scaffold proteins", Nano Lett. 2002, 2, 853-856.
J. Wang, S. Link, C.D. Heyes and M.A. El-Sayed, Comparison of the dynamics of the primary events of bacteriorhodopsin in its trimeric and monomeric states, Biophys. J. 83 (2002), pp. 1557-1566.
G. Bacher, R. Korner, A. Atrih, S.J. Foster, P. Roepstorff and G. Allmaier, Negative and positive ion matrix-assisted laser desorption/ionization time-of-flight mass spectrometry and positive ion nano-electrospray ionization quadrupole ion trap mass spectrometry of

(56) References Cited

OTHER PUBLICATIONS peptidoglycan fragments isolated from various bacillus species, J. Mass Spectrom. 36 (2001), pp. 124-139.
Sapra R et al, "Purification and characterization of a Membrane-Bound Hydrogenase from the Hyperthermophilic Archaeon *Pyrococcus furiosus*", J Bacteriol. 2000 182, (12) 3423-3428.
Sapra R et al,. "A simple energy-conserving system: Proton reduction coupled to proton translocation", J Bacteriol 2003, 100 (13), 7545-7550.
Pasini EM et al., In depth analysis of the membrane and cytosolic proteome of red blood cells, 2006 Blood, 108: 791-801.
G. Bacher et al., "Charge-reduced nano electrospray ionization combined with differential mobility analysis of peptides, proteins, glycoproteins, non covalent protein complexes and viruses", Journal of Mass Spectrometry 2001; 36: 1038-1052.
Goldet, G.; Wait, A. F.; Cracknell, J. A,; Vincent, K. A.; Ludwig, M.; Lenz, Friedrich, B.; Armstrong, F. A. , "Hydrogen Production under Aerobic Conditions by Membrane-Bound Hydrogenases from Ralstonia Species", Journal of the American Chemical Society 2008, 130, (33),1, 1106-1113.
Cracknell, J. A.; Vincent, K. A.; Ludwig, M.; Lenz, O.; Friedrich, B.; Armstrong, F. A., "Enzymatic oxidation of H2 in Atmosphere O2", Journal of the American Chemical Society 2007, 130,424-425.
Kovacs, K. L.; Maroti, G.; Rakhely, G., "A novel approach for biohydrogen production", International Journal of Hydrogen Energy 2006, 31, (1 1), 1460-1468.
Ho, D.; Chu, B.; Lee, H.; Brooks, E. K.; Kuo, K.; Montemagno, C. D., "Fabrication of biomolecule-copolymer hybrid nanovesicles as energy conversion systems", Nanotechnology 2005, 16, (12), 3120-3132.
Vincent, K. A.; Cracknell, J. A,; Lenz, O.; Zebger, I.; Friederich, B.; Armstrong, F., "Electrocatalytic hydrogen oxidation by an enyme at high carbon monoxide or oxygen levels", Proceedings of the National Academy of Sciences 2005,102, (47),16951-16954.
Dunn, R. J. et al., "Structure-functions studies on bacteriorhodopsin" Expression of the bacterio-opsin gene *Escherichia coli*, vol. 262, No. 19, pp. 9246-9254, Jul. 5, 1986.
Sonar, S et al., "Cell-Free Synthesis, Functional Refolding and Spectroscopic Characterization of Bacteriorhodopsin, an Integral Membrane Protein", Biochemistry, vol. 32, pp. 13777-13781, Oct. 25, 1993.
Kalmbach, R., et al., "Functional Cell-free synthesis of a seven helix membrane protein: In situ Insertion of Bacteriorhodopsin in Liposomes", J. Mol. Biol. vol. 371, pp. 639-648, 2007.
Bayburt, T. H., et al., "Assembly of single bacteriorhodopsin trimers in bilayer nandiscs", Archives of Biochemistry and Biophysics, pp. 215-222, 2006.
Bayburt, T. H., et al., "Reconstitution and Imaging of a Membrane Protein in a Nanometer-Size Phospholipid Bilayer" Journal of Structural Biology, pp. 37-44, 1998.
Forstner, M., et al., "Carboxyl-Terminal domain of Human Apolipoprotein E: Expression, Purification, and Crystallization", Protein Expression and Purification, vol. 17, pp. 267-272, 1999.
Morrow, J. A., et al., "Functional Characterization of Apolipoprotein E Isoforms Overexpressed in *Escherichia coli* ", Protein Expression and Purification, vol. 16,pp. 224-230, 1990.
Jayaraman, S., et al., "Structural Basis for Thermal Stability of Human Low-Density Lopoprotein", Biochemistry 44, pp. 3965-3971, 2005.
Gursky, O., et al., Compex of Human Apolipoprotein C-1 with Phospholipid: Thermodynamic or Kinetic Stability? Biochemistry 41, pp. 7373-7384, 2002.
Coleman, M., et al., "Asp 46 can substitute for Asp 96 as the Schiff Base Proton Donor in Bacteriorhodopsin", Biochemistry 34, pp. 15599-15606, 1995.
Klammt, C., et al., "High level cell-free expression and specific labeling of integral membrane proteins", Eur. J. Biochem, 271, pp. 568-580, 2004.
Klammt, C., et al., "Cell-free expression as an emerging technique for the large scale production of integral membrane protein" FEBS Journal, 273, pp. 4141-4153, 2006.
Sonar, S., et al., "A redirected proton pathway in the bacteriorhodopsin Mutan Tyr-57→Asp", The Journal of Biological Chemistry, vol. 269, No. 46, pp. 28851-28858, Nov. 18, 1994.
Klammt, C., et al., "Evaluation of detergents for the soluble expression of α-helical and β-barrel-type integral membrane proteins by a preparative scale individual cell-free expression system", FEBS Journal, pp. 6024-6038, 2005.
Camarero, J. A., et l., "Chemoselective Attachment of Biologically Active Protein to Surfaces by Expressed Protein Ligation and Its Application for Protein Chip Fabrication", J.A. Chem. Soc., vol. 126, pp. 14730-14731, 2004.
Rao, R.S., et al., "Comparison of Multiplexed techniques for detection of bacterial and Viral Proteins", Journal of Proteome Research, 3, pp. 736-742, 2004.
Segelke, B. W., et al., "Laboratory scale structural genomics", Journal of Structural and Functional Genomics 5, pp. 147-157, 2004.
Lu, B., et al., "Conformational reorganization of the four-helix bundle of human apolipoprotein E in Binding to Phospholipid", The Journal of Biological Chemistry , vol. 275, No. 27, pp. 20775-20781, Jul. 7, 2000.
Wientzek, M., et al., "Binding of Inspect Apolipophorin III to Dimyristoylphosphatidylcholine Vesicles", The Journal of Biological Chemistry, vol. 269, No. 6, pp. 4605-4612, 1994.
Forte T.M., "Electron microscope study on reassembly of plasma high density apoprotein with various lipids", Biochimi. Biophys. Acta, 248, pp. 381-386, 1971.
Abdulreda, M.H, Atomic Force Microscope Spectroscopy Reveals a Hemifusion Intermediate during Soluble N-Ethylmaleimide Sensitive Factor-Attachment Protein Receptors-Mediated Membrane Fusio, Biophysical Journal,vol. 94, pp. 648-655, Jan. 2008.
Beja, O. et al. Bacterial Phodopsin: Evidence for a New Type of Phototrophy in the Sea, Science, 2000, 2895.5486: 1902-1906.
Shih, A.Y. et al. Molecular Dynamics Simulations of Discoidal Bilayers Assembled from Truncated Human Lipoproteins, Biophysical J., 2005, vol. 88,pp. 548-556.
PCT International Search Report for PCT/US2008/063307 filed on Sep. 5, 2008 in the name of Lawrence Livermore National Security, LLC. Mailed: Oct. 29, 2008.
PCT Written Opinion for PCT/US2008/063307 filed on Sep. 5, 2008 in the name of Lawrence Livermore National Security, LLC. Mailed: Oct. 29, 2008.
Bayburt, T. H., et al., "Self-assembly of single integral membrane proteins into soluble nanoscale phospholipid bilayers", Protein Science vol. 12, No. 11, Nov. 2003, pp. 2476-2481, XP002498218 ISSN: 0961-8368.
Restriction Requirement issued for U.S. Appl. No. 12/118,530, filed May 9, 2008 in the name of Matthew A. Coleman et al.; mail date: Sep. 24, 2010.
Restriction Requirement issued for U.S. Appl. No. 12/118,530, filed May 9, 2008 in the name of Matthew A. Coleman et al.; mail date: Mar. 30, 2011.
Non-Final Office Action issued for U.S. Appl. No. 12/118,530, filed May 9, 2008 in the name of Matthew A. Coleman et al.; mail date: Aug. 30, 2011.
Final Office Action issued for U.S. Appl. No. 12/118,530, filed May 9, 2008 in the name of Matthew A. Coleman et al.; mail date: Jan. 25, 2012.
Advisory Action issued for U.S. Appl. No. 12/118,396, filed May 9, 2008 in the name of Matthew A. Coleman et al.; mail date: Jun. 7, 2012.
Final Office Action issued for U.S. Appl. No. 12/604,362, filed Oct. 22, 2009 in the name of Paul D. Hoeprich et al.; mail date: Dec. 4, 2012.
Non-Final Office Action mailed on Oct. 2, 2013 for U.S. Appl. No. 12/352,472, filed Jan. 12, 2009 in the name of Sarah E. Baker et al.

* cited by examiner

NANOLIPOPROTEIN PARTICLES AND RELATED COMPOSITIONS, METHODS AND SYSTEMS

CROSS REFERENCE TO RELATED APPLICATIONS

This application claims priority to U.S. Provisional Application entitled "Just-In-Time Vaccines Against Select Agent Biothreat Micro-organisms" Ser. No. 61/055,380, filed on May 22, 2008, the disclosure of which is incorporated herein by reference in its entirety.

STATEMENT OF GOVERNMENT GRANT

The United States Government has rights in this invention pursuant to Contract No. Contract No. DE-AC52-07NA27344 between the U.S. Department of Energy and Lawrence Livermore National Security, LLC, for the operation of Lawrence Livermore National Security.

TECHNICAL FIELD

The present disclosure relates to nanolipoprotein particles and related compositions, methods and systems.

BACKGROUND

Nanolipoprotein particles (NLPs) and other particles of nanoscale dimensions have been developed to support and carry target molecules.

In particular, a number of research groups have prepared recombinant high density lipoprotein particles (rHDL) as a cell membrane mimetic for incorporating membrane proteins—the latter consist of a hydrophobic moiety or membrane interacting region that associates with the nonpolar region of the lipid bilayer and portions that are hydrophilic and extend to both the interior and exterior regions.

According to this approach the target molecule is anchored to the nanolipoprotein particle through the hydrophobic moiety that is embedded within the lipid bilayer. The resulting molecular complex relies wholly on nonpolar interactions for stability in an overall aqueous environment.

In view of the above, incorporation of molecules which do not present a hydrophobic moiety for interaction within the lipid bilayer has been virtually impossible. Also, in view of the need to rely on nonpolar interactions for inclusion of the target molecule and stability of the nanolipoprotein particle, development of a nanolipoprotein particle comprising more than one target molecule has been challenging as well.

Accordingly, use of nanolipoprotein particles in applications, such as development of immunogenic compositions or development of systems for delivery of drugs or contrast agents, that require the inclusion of other molecules of interests, particularly soluble hydrophilic molecules, where the particle would ideally serve as a universal platform for supporting and carrying one or more target molecules of diverse chemical nature, has been particularly challenging.

SUMMARY

Provided herein, are nanolipoprotein particles and related compositions, methods and systems that in several embodiments are suitable to be used as nanoscale platforms for a plurality of molecules of any chemical nature, including hydrophilic molecules and molecules that do not present a hydrophobic moiety for interaction with the lipid bilayer of the nanoparticle.

According to a first aspect, a nanolipoprotein particle is described, that is suitable as a platform for a target molecule. The nanolipoprotein particle comprises a scaffold protein, a functionalized membrane forming lipid presenting an anchor compound substrate and optionally a membrane forming lipid. In the nanolipoprotein particle, the anchor compound substrate presented on the functionalized membrane forming lipid is capable of binding a corresponding anchor compound presented on the target molecule. The resulting functionalized nanolipoprotein particle is capable of binding a target molecule that presents or has been modified to present the anchor compound corresponding to the anchor compound substrate.

According to a second aspect, a nanolipoprotein particle comprising a hydrophilic target molecule is described. The nanolipoprotein particle comprises a scaffold protein, the hydrophilic target molecule attaching an anchor compound, and a functionalized membrane forming lipid attaching an anchor compound substrate and, optionally, a membrane forming lipid. In the nanolipoprotein particle, the hydrophilic target molecule is attached to the functionalized membrane forming lipid through binding of the anchor compound substrate with the anchor compound.

According to a third aspect, a nanolipoprotein particle comprising multiple target molecules is described. The nanolipoprotein particle is formed by assembling a functionalized membrane forming lipid, a scaffold protein and optionally a membrane forming lipid. In the nanolipoprotein particle each of the multiple target molecules attaches an anchor compound, and the functionalized membrane forming lipid attaches a corresponding anchor substrate compound. In the nanolipoprotein particle, the anchor compound binds the corresponding anchor compound substrate thus attaching each of the target molecules to the functionalized membrane forming lipid.

According to a fourth aspect, a nanolipoprotein particle is described that presents an active target molecule, such as an immunogen, a drug, a contrast agent or another molecule of interest. The nanolipoprotein comprises the active target molecule attaching a first anchor compound, a membrane recognition element attaching a second anchor compound, scaffold protein, a first functionalized membrane forming lipid attaching an anchor compound substrate and a second functionalized membrane forming lipid attaching a second anchor compound substrate. In the nanolipoprotein particle, the active target molecule is attached to the functionalized membrane forming lipid through binding of the anchor compound with the anchor compound substrate. In the nanolipoprotein particle, the nanolipoprotein is configured to present the active target molecule and the membrane recognition element on said nanolipoprotein particle.

According to additional aspects, compositions, (and in particular pharmaceutical compositions and vaccines), methods and systems, comprising, forming and using the nanolipoprotein particles herein described are also provided in the present disclosure. Methods and systems to perform an assay on a target molecule and/or to deliver a target molecule based on the nanolipoprotein particles of the present disclosure, are also described.

The nanolipoprotein particles, compositions, methods and systems herein described can be used in several embodiments as a universal platform for support, delivery and presentation of molecules of any chemical nature, which can present or not present a hydrophobic moiety for interaction with the lipid bilayer, which include but are not limited to proteins, polypeptides, toxins, carbohydrates, lipids, fatty acids, and small organic molecules (e.g. dyes, drugs, plasticizers, and the like).

Additionally, the nanolipoprotein particles, compositions, methods and systems herein described can be used in several embodiments to support, deliver and/or present multiple target molecules In particular, in several embodiments the nanoparticles herein described can be used in connection with applications where multivalency of a target molecule on a controllable, discrete, and characterizable nanoscale platform is desired.

Furthermore, the nanolipoprotein particles, compositions, methods and systems herein described can be used in several embodiments in connection with delivery and presentation of a chemically and/or biologically active target molecule performed to detect and/or enhance an individual response to the active target molecule.

In particular, the nanolipoprotein particles, compositions, methods and systems herein described can be used in several embodiments as a particulate platform for the delivery and presentation of immunogens, which are presented on the functionalized bilayer of the nanolipoprotein particles.

Also in several embodiments, the nanolipoprotein particles, compositions, methods and systems herein described can be used to deliver drugs or other molecules of interest, to specific target cells in an individual.

Also in several embodiments, the nanolipoprotein particles can be used as multivalent affinity platforms for biosensors and diagnostics, whereby NLPs presenting multiple affinity reagents can interact with multiple target molecules or engage in multivalent recognition of a single, larger target.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and example sections, serve to explain the principles and implementations of the disclosure.

FIG. 2A shows a schematic illustration of production of an NLP platform according to an embodiment herein described; note, specifically inclusion of functionalized anchor substrate lipid (in this case nickel-chelating lipids); FIG. 2B shows a schematic illustration of production of an anchor-bearing immunogenic protein according to an embodiment herein described; FIG. 2C shows a schematic illustration of production of an immunogenic NLP from the NLP platform and the anchor-bearing immunogenic protein according to an embodiment herein described FIG. 3 shows an electrophoresis gel demonstrating conjugation of the NiNLP platform with a His-tagged Env protein from West Nile virus (WNV). NiNLPs incubated with His-tagged ENV at room temperature for 30 minutes were analyzed by denaturing SDS-PAGE. Total sample (T) was compared to retentate fraction (R) after size-exclusion partitioning using a 100 kDa MWCO membrane filter, enabling NiNLPs (>400 kDa) to be separated from unconjugated ENV (50 kDa). Addition of EDTA abrogates any interaction between the protein and the NiNLP, demonstrating that conjugation is due to specific interaction of His-tag and chelated nickel.

FIG. 3A shows NiNLPs alone, FIG. 3B shows NiNLPs+His-tagged protein), and FIG. 3C shows NiNLPs+His-tagged protein in the presence of EDTA. Scale bar is 50 nm. A height increase is observed only when the His-tagged protein is incubated with NiNLP in the absence of EDTA. Discoidal morphology of NiNLPs is demonstrated by AFM, whereby the NiNLP diameter is greater than the NiNLP height.

DETAILED DESCRIPTION

Figure 1:
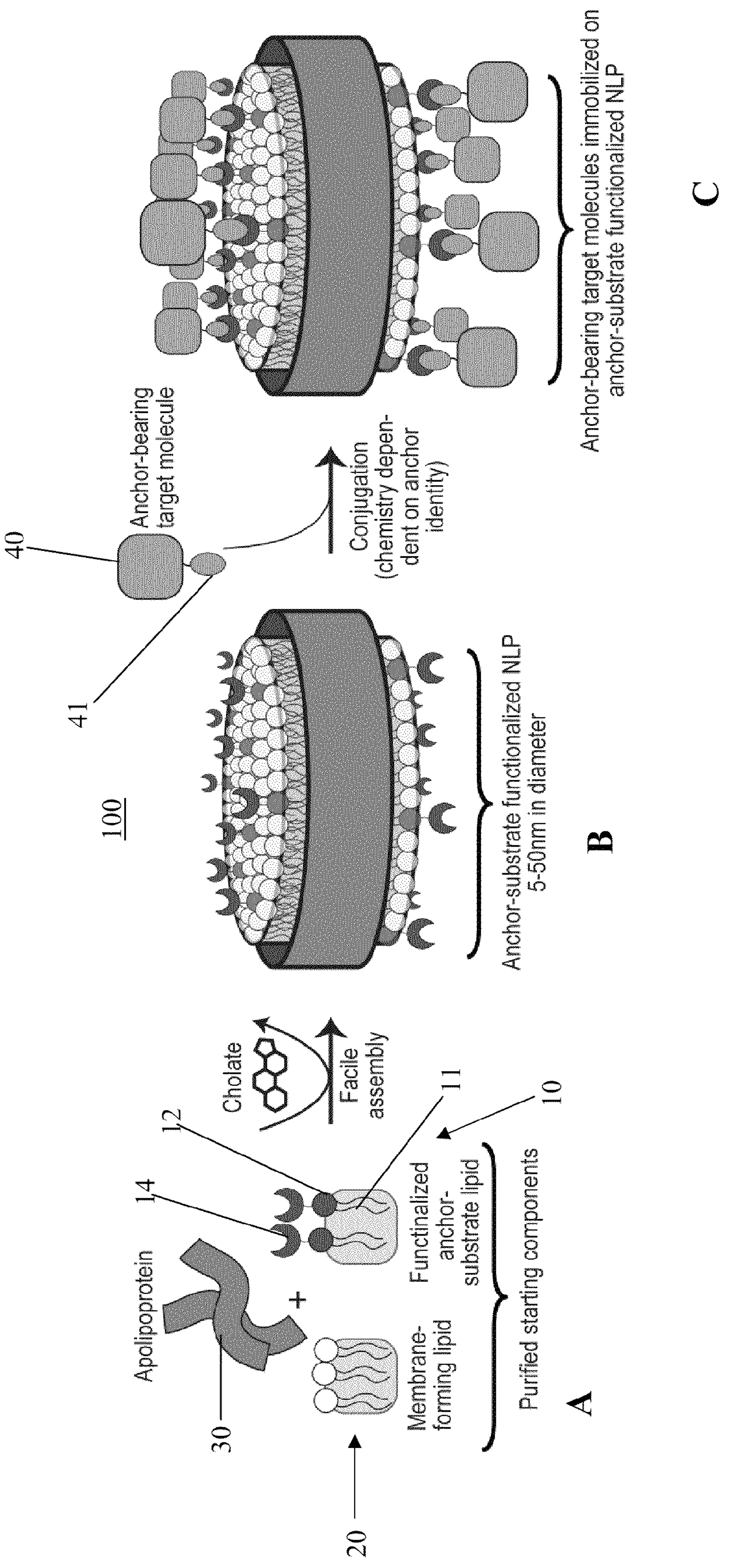
FIG. 1 shows a schematic illustration of assembly of a nanolipoprotein particle comprising a functionalized membrane forming lipid according to an embodiment here described.

Nanolipoprotein particles are herein described that comprise a functionalized membrane forming lipid presenting an anchor compound substrate for binding with a target molecule.

The terms "nanolipoprotein particle", "rHDL", or "NLP" as used herein indicates a supramolecular complex formed by a membrane forming lipid and a scaffold protein. In particular, nanolipoprotein particles are nano-sized particles comprised of partitioned bilayers of membrane forming lipid stabilized by peripherally associated scaffold proteins which range in size between about 5 and about 50 nm. Nanolipoprotein size is detectable using techniques such as nondenaturing gradient gel electrophoresis (NDGGE) and size exclusion chromatography (SEC) and additional techniques identifiable by a skilled person upon reading of the present disclosure. NLPs are obtainable by allowing solubilized membrane forming lipids and scaffold protein to self-assemble in an aqueous environment in a molar ratio of membrane forming lipid to scaffold from about 15:1 up to about 400:1.

Solubilization of the membrane forming lipids can be performed by using a detergent, such as cholate, which is associated with the lipids. Removal of this detergent allows self assembly of the membrane forming lipid and the scaffold protein. Alternatively, or in addition, the membrane forming lipids (in the form of small unilamellar vesicles) and scaffold protein can be subjected to temperature cycles according to procedures known in the art.

Exemplary procedures to perform self assembly of NLPs are described in art, for example in References 4 and 5, and in other references identifiable by a skilled person. NLPs prepared using these procedures are discoidal in morphology (i.e. non-spheroidal). The NLP height is correlated to the bilayer thickness of the membrane forming lipid used. Typically, the bilayer thickness is between about 4 and about 7 nanometers, and is dependent on the identity of the membrane forming lipid. The diameter of the NLPs can be between about 5 and about 50 nanometers, typically ranging between about 10 and about 25 nanometers. By nature of this morphology, a planar surface is present on both sides of the lipid bilayer. Size, structure and discoidal shape of an NLP can be detected by several techniques such high resolution imaging and sizing techniques such as atomic force microscopy (AFM), transmission electron microscopy (TEM), ion mobility spectrometry and additional techniques suited to analyze particles in the low nanometer size regime identifiable by a skilled person upon reading of the present disclosure [Refs. 4 and 10].

The term "membrane forming lipid" or "amphipathic lipid" as used herein indicates a lipid possessing both hydrophilic and hydrophobic properties that can, in an aqueous environment and in the presence of a scaffold protein, assemble in a lipid bilayer structure that consists of two opposing layers of amphipathic molecules known as polar lipids. Each polar lipid has a hydrophilic moiety, i.e., a polar group such as a derivatized phosphate or a saccharide group, and a hydrophobic moiety, i.e., a long hydrocarbon chain(s). Exemplary polar lipids include phospholipids, sphingolipids, glycolipids, ether lipids, and sterols. Amphipathic lipids include but are not limited to membrane lipids, i.e. amphipathic lipids that are constituents of a biological membrane, such as phospholipids like dimyristoylphosphatidylcholine (DMPC) or dioleoylphosphoethanolamine (DOPE) or dioleoylphosphatidylcholine (DOPC). In some embodiments, the membrane forming lipid can be a biological molecule, i.e. a molecule produced by a living organism including unicellular organism, such as bacteria or yeasts, and multicellular such as animals, including mammals and humans, and plants. In some embodiments, the membrane forming lipids can consist of non-lipid amphipathic molecules, for example diglycerol tetraethers, cholesterol, ergosterol, and the like.

The term "scaffold protein" as used herein indicates any protein that is capable of self assembly with an amphipathic lipid in an aqueous environment, organizing the amphipathic lipid into a bilayer, and include but are not limited to apolipoproteins, apolipophorins, derivatives thereof (such as truncated and tandemly arrayed sequences) and fragments thereof (e.g. peptides), such as apolipoprotein E4 22K fragment, apolipophorin III, apolipoprotein A-1 and the like. The term "derivative" as used herein indicates a chemical or biological substance that is related structurally to another substance and derivable, at least theoretically, from the another substance through a modification of the another substance. In particular, if a first compound is a derivative of a second compound and the second compound is associated with a chemical and/or biological activity, the first compound differs from the second compound for at least one structural feature, while retaining (at least to a certain extent) the chemical and/or biological activity of the second compound and at least one structural feature (e.g. a sequence, a fragment, a functional group and others) associated thereto. A skilled person will be able to identify, on a case by case basis and upon reading of the present disclosure, structural feature of the second compound that has to be maintained in the first compound to retain the second compound chemical and/or biological activity as well as assays that can be used to prove retention of the chemical and/or biological activity .

The term "protein" as used herein indicates a polypeptide with a particular secondary and tertiary structure. The term "polypeptide" as used herein indicates an organic polymer composed of two or more amino acid monomers and/or analogs thereof. Accordingly, the term "polypeptide" includes amino acid polymers of any length including full length proteins and peptides, as well as analogs and fragments thereof. A polypeptide of three or more amino acids can be a protein oligomer or oligopeptide. As used herein the term "amino acid", "amino acid monomer", or "amino acid residue" refers to any of the twenty naturally occurring amino acids including synthetic amino acids with unnatural side chains and including both D and L optical isomers. The term "amino acid analog" refers to an amino acid in which one or more individual atoms have been replaced, either with a different atom, isotope, or with a different functional group but is otherwise identical to its natural amino acid analog.

In the nanolipoprotein particle here described at least a portion or all of the membrane forming lipid is functionalized with an anchor substrate compound that is presented for binding with a target molecule. The terms "functionalize" and "functionalization" as used herein, indicates the appropriate chemical modifications of a molecular structure (including a substrate or a compound) resulting in attachment of a functional group to the molecular structure. The term "functional group" as used herein indicates specific groups of atoms within a molecular structure that are responsible for the characteristic chemical reactions of that structure. Exemplary functional groups include, hydrocarbons containing halogen groups, containing oxygen groups, containing nitrogen groups, containing phosphorus groups and containing sulfur groups, all identifiable by a skilled person.

In particular, the ratio between functionalized membrane forming lipid and membrane forming lipids is dependent on the identity of the functionalized membrane forming lipid, and it can be as low as 1% or even lower and as high as 100% as NLPs have been successfully formed with 100% functionalized membrane forming lipid such as DOGS-NTA-Ni (1,2-di-(9Z-octadecenoyl)-sn-glycero-3-[(N-(5-amino-1-carboxypentyl)iminodiacetic acid)succinyl] (nickel salt)). This suggests that NLPs can be formed with any percentage of functionalized membrane forming lipid (from 0 to 100%), depending on the specific functionalized membrane forming lipid used.

In general, assembly of NLPs can be accomplished with a wide range of ratios of total membrane forming lipids to scaffold proteins. We have successfully formed NLPs with lipid to scaffold molar ratios of about 15:1 up to about 400:1. A typical assembly uses a lipid to protein molar ratio of about 100:1.

The term "anchor compound substrate" as used herein indicates a functional group capable to bind a corresponding functional group, herein also indicated as anchor compound, presented on another molecule, and in particular on a target molecule to be attached in the nanolipoprotein particle.

The term "bind", "binding", "conjugation" as used herein indicates an attractive interaction between two elements which results in a stable association of the element in which the elements are in close proximity to each other. If each element is comprised in a molecule the result of binding is typically formation of a molecular complex. Attractive interactions in the sense of the present disclosure includes both non-covalent binding and, covalent binding. Non-covalent binding as used herein indicates a type of chemical bond, such as protein protein interaction, that does not involve the sharing of pairs of electrons, but rather involves more dispersed variations of electromagnetic interactions. Non-covalent bonding includes ionic bonds, hydrophobic interactions, electrostatic interactions, hydrogen bonds, and dipole-dipole bonds. Electrostatic interactions include association between two oppositely charged entities. An example of an electrostatic interaction includes using a charged lipid as the functional membrane lipid and binding an oppositely charged target molecule through electrostatic interactions.

Anchor compound substrates and corresponding anchor compound capable of binding through non-covalent binding include but are not limited to those listed in Table 1 below.

TABLE 1

Non-Covalent Interactions

| Anchor (on a target molecule) | Anchor substrate (on functionalized lipid within NLP bilayer) |
|---|---|
| Poly-histidine (2-10 residues) | Chelated metal cations |
| 2-10 residue polypeptide | $Ni^{2+}$, $Co^{2+}$, $Cu^{2+}$, $Zn^{2+}$ chelated on NTA, IDA |
| Poly-arginine (5-6 residues) | Negatively charged surface |
| 5-6 residue polypeptide | e.g. carboxylates, phosphates, sulfonates |
| Proteins | Biological tags |
| Avidin (Streptavidin, neutravidin) | Biotin |
| Glutathione S-transferase (GST) fusion proteins | Glutathione |
| Strep-Tactin | Strep-tag II |

A covalent bond is instead a form of chemical bonding that is characterized by the sharing of pairs of electrons between atoms, or between atoms and other covalent bonds. In short, attraction-to-repulsion stability that forms between atoms when they share electrons is known as covalent bonding. Covalent bonding includes many kinds of interaction, including σ-bonding, π-bonding, metal to non-metal bonding, agostic interactions, and three-center two-electron bonds.

Anchor compound substrates and corresponding anchor compounds capable of binding through covalent binding include but are not limited to those listed in Table 2 below.

TABLE 2

Covalent Interactions

| Anchor (or anchor substrate) | Anchor substrate (or anchor) |
|---|---|
| Amine-reactive moieties | Amines |
| Active esters (e.g. succinimidyl, tetrafluorophenyl) | |
| Carbodiimide (+/− NHS)-Carboxylic acids | |
| Isothiocyanates | |
| Sulfonyl chlorides | |
| Dichlorotriazines | |
| Aryl halides | |
| Acyl azides | |
| Thiol-reactive reagents | Sulfhydryls |
| Maleimides (and derivatives) | |
| Haloacetamides (e.g. iodoacetamide) | |
| Pyridyldithio-propionate | |
| Thiosulfates | |
| Azides ("Click Chemistry" - formation of 1,2,3-triazol groups, ref. 7) | Acetylenes |
| Hydrazines/hydroxylamines/aromatic amines | Aldehydes and ketones |

Accordingly, exemplary functionalized membrane forming lipids include, but not limited to chelated metal-bearing lipids, azide bearing lipids, maleimide bearing lipids, quaternary amine bearing lipids, carboxylate bearing lipids, propargyl bearing lipids, biotin bearing lipids, streptavidin and/or avidin bearing lipids, S-protein bearing lipids, and the like.

In some embodiments, binding or conjugation of the anchor compound can be performed by chelation. The term "chelation" as used herein indicates the binding or complexation of a bi- or multidentate ligand with a single metal ion. In particular, in some embodiments, the bi or multi-dentate ligand is part of the lipid and is capable of binding a metal ion. The ligands, which are often organic compounds, are called chelants, chelators, chelating agents, or sequestering agents. Chelating agents form multiple bonds with a single metal ion. The term "chelants" as used herein indicates a molecule that forms a stable complex with certain metal ions. Examples of chelating moieties include, but are not limited to, nitrilotriacetic acid (NTA), iminodiacetic acid (IDA), and diethylenetriamine penta-acetic acid (DTPA).

In the nanolipoprotein particle herein described the anchor substrate compound is attached to the functionalized membrane forming lipid so that upon assembly of the functionalized membrane forming lipid in the nanolipoprotein particle, the anchor substrate compound is presented on the nanolipoprotein particle. Similarly, the anchor compound is attached to a target molecule to be presented on said target molecule.

The term "attach" or "attached" as used herein, refers to connecting or uniting by a bond, link, force or tie in order to keep two or more components together, which encompasses either direct or indirect attachment such that for example where a first compound is directly bound to a second compound or material, and the embodiments wherein one or more intermediate compounds, and in particular molecules, are disposed between the first compound and the second compound or material.

The term "present" as used herein with reference to a compound or functional group indicates attachment performed to maintain the chemical reactivity of the compound or functional group as attached. Accordingly, a functional group presented on a molecule such as a functionalized membrane forming lipid, is able to perform under the appropriate conditions the one or more chemical reactions that chemically characterize the functional group.

In particular, in several embodiments the functionalized membrane forming lipid are functionalized to present the anchor substrate compound on an hydrophilic moiety of the membrane forming lipid to ensure presentation of the anchor substrate compound on a surface of the nanolipoprotein particle. The term "surface" as used herein indicates the exterior or upper boundary of a body or object. In particular with reference to the NLPs the term "surface" indicates they are defined by the discoidal faces. Surfaces of the NLPs form the hydrophilic portion of the NLP.

Successful binding of the target molecule to the NLP can be readily verified and quantified through a range of techniques that include but are not limited to ultraspin filtration, size exclusion chromatography, fluorescence correlation spectroscopy, cantilever-based sensing, force spectroscopy, fourier transform infrared spectroscopy, surface plasmon resonance, total internal reflection fluorescence, raman spectroscopy and additional techniques identifiable by a skilled person. In addition, binding specifically to the surface can be verified using atomic force microscopy and transmission electron microscopy and additional techniques identifiable by a skilled person.

The structure of nanolipoprotein particles herein described is illustrated in FIG. 1 which shows a schematic representation of an NLP assembly comprising a functionalized membrane forming lipid according to some embodiments herein described.

As exemplified in the illustration of FIG. 1 panels A and B, purified starting components are provided that comprise a functionalized membrane forming lipid (10), a membrane forming lipid (20), and a scaffold protein (30). The functionalized membrane forming lipid (10) comprises a hydrophobic moiety (11) and a hydrophilic moiety (12) and attached an anchor compound substrate (14) capable of binding to a corresponding anchor compound (41) presented on the target molecule (40) of interest. In particular, the anchor compound substrate (14) is presented on the hydrophilic moiety (12) of the functionalized membrane forming lipid (10). The functionalized membrane forming lipid (10), the membrane forming lipid (20), and the scaffold protein (30) are contacted for a time and under conditions to allow assembly of the functionalized membrane forming lipid. In particular, spontaneous interaction of purified scaffold proteins, e.g. apolipoproteins, and membrane forming lipids under appropriate conditions results in formation of lipoprotein particles with the nanometer-sized dimensions that are herein identified as NLPs.

In the illustration of FIG. 1 Panel B the nanolipoprotein particle (100) formed by the assembly of the functionalized membrane forming lipid (10), the membrane forming lipid (20) and the scaffold protein (30) is configured to present the anchor compound substrate (14) on a surface of the nanolipoprotein particle. In particular, as shown in the illustration of FIG. 1 anchor compound substrate moieties are appended to the headgroups of the functionalized membrane forming lipid, and are presented into solution.

The amount of anchor-substrate moieties on the NLP bilayer surface can be controlled by the input ratios of membrane-forming and functionalized anchor-substrate lipids during assembly, allowing control of target molecule loading on NLP. Generally, if 10 molar percent of the total lipid used for an assembly is a functionalized membrane forming lipid, then approximately 10 molar percent of the total lipid within the NLP lipid bilayer will be functionalized membrane forming lipid. This has been verified in the case of NLPs prepared with 90 molar percent DMPC and 10 molar percent of DOGS-NTA-Ni. The feed ratio to incorporated ratio of the anchor substrate moiety can further be quantitatively assesses after completion of NLP assembly using normal phase and reverse phase high performance liquid chromatography and subsequent ratios can be adjusted to achieve the desired input ratio.

Although other reagents might be added according to the desired experimental design, no other reagents have to be added to impart functionality to the NLPs since the functionalized membrane forming lipids containing the necessary reactive group for conjugation As schematically shown in FIG. 1 Panel C, a target molecule (40) bearing the appropriate corresponding anchor compound (41) (an anchor compound able to bind and accordingly be defined as complementary to the anchor-compound substrate (14)) can be attached on the NLP bilayer surface of the NLP (100).

In particular, the target molecule (40) and the nanolipoprotein (100) are contacted for a time and under conditions to allow binding of the anchor compound (41) with the anchor compound substrate (14), which depends on the conjugation chemistry between the anchor compound and the anchor substrate compound.

In particular, attachment of target molecules to nanolipoprotein particles can be accomplished using any number of functionalization strategies and orientations. For example, using click chemistry, an acetylene-functionalized lipid can be conjugated with an azide-functionalized protein, or an azide-functionalized lipid can be conjugated with an acetylene-functionalized protein [Ref. 9].

In particular, the conjugation of azides with acetylenes (herein also indicated as click chemistry) can be achieved in buffered aqueous solution over a broad pH range for about 1 to about 24 hours to form a covalent 1,2,3-triazole. This reaction can be catalyzed by copper(I), typically introduced by addition of copper(II) in the presence of a reductant (e.g. ascorbic acid) to generate copper(I) in situ.

In other exemplary embodiments where attachment of a polyhistidine functionalized target molecule to a bivalent metal functionalized lipid is desired, conjugation of the polyhistidine anchor compound to the chelated metal ($Ni^{2+}$, $Co^{2+}$, $Cu^{2+}$, $Zn^{2+}$) anchor compound substrate (NTA or IDA) can be achieved over the course of an incubation ranging in time from about 5 minutes to about 2 hours at room temperature without the need of any additional components. According to this approach, no additional chelating agents (e.g. EDTA) are present in solution.

In other exemplary embodiments, where attachment of a poly-arginine functionalized target molecule to a an anionic functionalized lipid is desired, conjugation of the poly-arginine anchor compound to an anionic surface anchor compound substrate can be achieved over the course of an incubation ranging in time from about 5 minutes to about 2 hours at room temperature without the need of any additional components.

In other exemplary embodiments where attachment of a target molecule functionalized with a protein anchor, to a lipid functionalized with a cognate biological tag is desired, conjugation of the protein anchor compounds, e.g. avidin (and derivatives such as neutravidin and the like,), glutathione S-transferase (GST) and Strep-Tactin, to the cognate biological tag anchor compound substrates biotin, glutathione, and strept-tag II, respectively, can be achieved over the course of an incubation ranging in time from about 5 minutes to about 2 hours at room temperature without the need of any additional components.

In other exemplary embodiments where attachment of a target molecule to a functionalized lipid is performed through conjugation of active esters to amine, conjugation of the active esters to the amines is achieved in amine-free buffered aqueous solution at a pH of about 7.0 for about 1 to about 24 hours to form a covalent amide bond. Reaction can then be quenched upon addition of free amines at neutral to basic pH. No other reagents are needed to perform conjugation.

In other exemplary embodiments where attachment of a target molecule to a functionalized lipid is performed through conjugation of carboxylic acids to amine, conjugation of the carboxylic acids to the amines can be achieved by activating the carboxylic acid to an active ester, using commercially available reagents, e.g. N-hydroxysuccinimide (NHS). This can be accomplished by combining the NHS and a dehydrating agent (e.g. carbodiimides like 1-Ethyl-3-(3-dimethylaminopropyl)carbodiimide (EDC)) with the target carboxylic acid. The EDC reacts with the carboxylic moiety to form a transient amine-reactive O-acylisourea, whereby NHS converts the amine-reactive O-acylisourea to an amine-reactive NHS-ester. A covalent amide bond is can then be achieved in amine-free buffered aqueous solution at a pH of 7.0 for 1 to 24 hours. Reaction can then be quenched upon addition of free amines at neutral to basic pH.

In other exemplary embodiments where attachment of a target molecule to a functionalized lipid is performed through conjugation of isothiocyanate to amine, conjugation of the isothiocyanates to the amines is achieved in amine-free buffered aqueous solution at a pH of about 7.0 for about 1 to about 24 hours to form a covalent thiourea. Reaction can then be quenched upon addition of free amines at neutral to basic pH. According to this approach, no other reagents are needed to obtain conjugation.

In other exemplary embodiments where attachment of a target molecule to a functionalized lipid is performed through conjugation of maleimides (and maleimide derivatives) to sulfhydryls, conjugation of the maleimides (and maleimide derivatives) to sulfhydryls can be achieved in thiol-free buffered aqueous solution at a pH between about 6.5 and about 0.5 for about 1 to about 24 hours to form a covalent thioether linkage. Maleimides can then be quenched at the completion of the reaction by the addition of free thiol. Reducing agents (e.g. tris(2-carboxyethyl)phosphine) may be used to produce free, reactive sulfhydryls, which may also be stabilized by the addition of ethylenediaminetetraacetic acid (EDTA).

In other exemplary embodiments where attachment of a target molecule to a functionalized lipid is performed through conjugation of halocetamide to sulfhydryls, conjugation of the haloacetamides to the sulfhydryls can be achieved in thiol-free buffered aqueous solution at a pH of about 8.3 for about 1 to about 24 hours to form a covalent thioether linkage by nucleophilic substitution of the halogen with the thiol. According to this approach no other reagents are needed to achieve conjugation.

In other exemplary embodiments where attachment of a target molecule to a functionalized lipid is performed through conjugation of pyridyl disulfides to sulfhydryls, conjugation of the pyridyl disulfides to the sulfhydryls can be achieved in thiol-free buffered aqueous solution over a broad pH range for about 1 to about 24 hours to form disulfide bonds. According to this approach no other reagents are needed to achieve conjugation.

In other exemplary embodiments where attachment of a target molecule to a functionalized lipid is performed through conjugation of thiosulfate to sulfhydryls, conjugation of thiosulfates with sulfhydryls can be achieved in thiol-free buffered aqueous solution over a broad pH range for 1 to 24 hours to form disulfide bonds. No other reagents are needed.

In all those exemplary embodiments, conjugation of the target molecule with the functionalized NLP can be monitored using techniques/methods such as the ones indicated.

In some embodiments, attachment of one or more target molecule in a same functionalized NLP can be performed using different compounds and corresponding anchor substrate for a same NLP where the selection of compatible anchor/anchor substrate pair can be performed by the skilled person in view of the target molecule(s) to be attached, the chemistry of the compounds involved and the experimental design.

In particular, compatibility of the anchor/substrate pair of choice with all the NLP components has to be considered in selecting a suitable NLP for attaching a target molecule of interest. For example, in some embodiments amine-based conjugation is not compatible with certain scaffold proteins. A skilled person will be able to identify and sort components according to a desired experimental design.

Target molecules that can be attached according to the method here described include any molecule of interest of any chemical nature, provided that those molecules present (or are modified to present) an anchor compound for binding with the anchor compound substrate on the NLP.

Using this approach, target molecules can be immobilized on the surface of the lipid bilayer, obviating the need for a target molecule to contain a hydrophobic region for direct interaction with the hydrophobic core of the NLP bilayer.

This has been successfully demonstrated by Applicants using the specific chelated nickel:polyhistidine-tag interaction (see exemplary procedures illustrated in the Examples 1 and 2), the specific biotin-neutravidin interaction (see exemplary procedures illustrated in the Examples 6 and 7) and the maleimide-thiolate (see exemplary procedures illustrated in the Examples 8 and 9). A skilled person will be able to derive corresponding procedures for other anchor/substrate compounds interaction on the basis of the present disclosure also with reference to the prophetic Examples 9 to 13 herein provided for guidance purposes with no intention of being limiting.

This strategy, unlike previous approaches, provides a means for attaching targets of interest that are not limited to a hydrophobic molecule (e.g. membrane protein or nonpolar drug) i.e. molecules presenting a hydrophobic moiety configured to allow stable interaction with the NLP lipid bilayer and can now include molecules of any chemical nature protein, peptides, oligonucleotides, small molecules, carbohydrates, metal ions, and additional molecules identifiable by a skilled person upon reading of the present disclosure.

Exemplary protein molecules include viral proteins (such as envelope protein of West Nile virus), bacterial proteins (such as *B. anthracis* protective antigen), animal proteins (such as TSG101), plant proteins, fungal proteins, archaea proteins.

Exemplary polynucleotides include, but are not limited to, aptamers, DNA, RNA, siRNA, microRNAs.

Exemplary small molecules include, but are not limited to, quorum sensing factors, metabolites, active pharmaceutical ingredients (APIs).

In particular, in several embodiments, the NLPs herein described allow attachment of a hydrophilic target molecule. The term hydrophilic target molecule as used herein indicates a molecule that contain a large regions or structural domain that are charge-polarized and capable of hydrogen bonding, to the extent of enabling the molecule to dissolve more readily in water than in oil or other hydrophobic solvents.

Additionally, in several embodiments, the NLPs herein described can be used to attach multiple (i.e. 4 or more) target molecules on the lipid bilayer surface. More particularly, in several embodiments multiple copies of a same target molecule can be attached to the NLP. This greatly opens the door for applications where multivalency of a target molecule on a controllable, discrete, and characterizable nanoscale platform is desired or required. Furthermore, the identity of the molecule to be immobilized on the NLP is not limited to a hydrophobic molecule (e.g. membrane protein or nonpolar drug) as is the case with all prior art examples, and can now include protein, peptides, oligonucleotides, small molecules, carbohydrates, metal ions, etc.

In several embodiments, the NLPs herein described can contain multiple, different functionalized lipids that are specific for different target molecules. More particularly, in several embodiments multiple copies of a same target molecule can be attached to the NLP. This greatly opens the door for applications where multiple, different types of target molecules are desired on a controllable, discrete, and characterizable nanoscale platform is desired or required. Furthermore, the identity of the molecule to be immobilized on the NLP is not limited to a hydrophobic molecule (e.g. membrane protein or nonpolar drug) as is the case with all prior art examples, and can now include protein, peptides, oligonucleotides, small molecules, carbohydrates, metal ions, etc.

In several embodiments, the target molecule is an active target molecule. An "active target molecule" in the sense of the present description is a molecule capable of exhibiting a chemical and/or biological activity. The term "chemical activity" as used herein indicates the ability of the molecule to perform a chemical reaction. The term biological activity as used herein indicates the ability of the molecule to affect a living matter. Exemplary active target molecules comprise an immunogen, a drug, a contrast agent, a molecular recognition element and any other molecules associated with a chemical and/or biological activity of interest.

In several embodiments, when the target molecule is an active target molecule the target molecule is configured to present the anchor compound in a position that allows, upon binding the NLP, presentation of the active target molecule on the nanolipoprotein particle.

In several embodiments, NLPs herein described can be formed with a variety of phospholipids including but not limited to: dimyristoylphosphatidylcholine (DMPC), dioleoylphosphoethanolamine (DOPE), dioleoylphosphatidylcholine (DOPC), and dioleoylphosphoserine (DOPS).

In several embodiments, NLPs herein described can be formed with apolipoproteins that include human ApoE4 22K and insect lipophorins from *Bombyx mori* and *Manduca sexta.*

In several embodiments the functionalized membrane forming lipid can include but is not limited todioleoyl-glycero-3-[(N-(5-amino-1-carboxypentyl)iminodiacetic acid) succinyl] (DOGS-NTA) and DOGS-NTA(Ni), 1,2-di-(9Z-octadecenoyl)-sn-glycero-3-phosphoethanolamine-N-[4-(p-maleimidophenyl)butyramide] (18:1 MPB PE), and 1,2-di-(9Z-octadecenoyl)-sn-glycero-3-phosphoethanolamine-N-(cap biotinyl) (sodium salt).

In particular, in some of those embodiments, where binding is performed by interaction with a chelated bivalent metal ion, the chelant is a modified lipid molecule, e.g. dioleoyl-glycero-3-[(N-(5-amino-1-carboxypentyl)iminodiacetic acid)succinyl] (DOGS-NitriloTriaceticAcid) and DOGS-NTA(bivalent metal ion) to which His-tagged proteins can be specifically and directly conjugated.

Embodiments based on the bivalent metal ion-chelating ability of NiNLPs allow conjugation of any (His)-tagged protein, opening the door to thousands of potential target molecules. Bivalent metal ions comprise Ni and additional transition metals bound or chelated by poly-histidine sequences. Exemplary bivalent metal ions include but are not limited to $Co^{2+}$, $Ni^{2+}$, $Cu^{2+}$ and $Zn^{2+}$. Corresponding poly-histidine tags can be comprised at either one of the ends of the target molecule to be attached. For example a His-tag can be added at either the N- or C-terminus of recombinantly expressed proteins to enable rapid isolation and purification [See Ref. 6].

In other embodiments, the membrane forming lipid can be functionalized to contain an azide group that can react with a protein specifically modified to contain a propargyl group. The reaction product between the azide and acetylene group forms a 1,2,3-triazole moiety. The product of this cycloaddition reaction or "click chemistry" is a covalent association between the target molecule and NLP [Ref. 7].

Still other embodiments a thiol group is added to the target molecule and is then reacted with a maleimide group presented on a functionalized membrane forming lipid. Maleimide bearing lipids (functionalized anchor substrate lipid), are available commercially. In this case, an anchor-bearing molecule would be configured to present a free thiol group that could add to the maleimide moiety forming a covalent bond [Ref 8].

In particular, metal chelating lipids, such as 1,2-di-(9Z-octadecenoyl)-sn-glycero-3-[(N-(5-amino-1-carboxypentyl) iminodiacetic acid)succinyl] (ammonium salt), and the like, that are suitable in forming NLPs herein described, are commercially available or synthesizable by a skilled person using techniques known in the art. In embodiments where metal chelating lipids are used in a functionalized NLP, the corresponding target molecules are configured to contain a poly-histidine tag for conjugation. Attachment of a polyhistidine tag to the target molecule can be achieved through molecular biological approaches and techniques identifiable by a skilled person.

Also negatively charged headgroup lipids, such as phosphatidic acid, phosphatidylserine, phosphatidylglycerol-bearing lipids, and the like, that are suitable in forming NLPs herein described are commercially available or synthesizable by a skilled person using techniques known in the art. In embodiments where negatively charged headgroup lipids are used in a functionalized NLP, the corresponding target molecules are configured to contain a polyarginine tag for conjugation. Attachment of a polyarginine tag to the target molecule can be achieved through molecular biological approaches and techniques identifiable by a skilled person. Further, target molecules that are inherently positively charged require no further modification.

Positively charged headgroup lipids, such as 1,2-di-(9Z-octadecenoyl)-3-trimethylammonium-propane (chloride salt), and the like, that are suitable in forming NLPs herein described are commercially available or synthesizable by a skilled person using techniques known in the art. In embodiments where positively charged headgroup lipids are used in a functionalized NLP, the corresponding target molecules are configured to contain an overall negative charge for conjugation sufficient to allow binding with the headgroup. In some of those embodiment the negatively charges molecule require no further modification to allow conjugation with the functionalized NLP.

Biotinylated lipids, such as 1,2-dihexadecanoyl-sn-glycero-3-phosphoethanolamine-N-(biotinyl) (sodium salt), and the like, that are suitable in forming NLPs herein described are commercially available or synthesizable by a skilled person using techniques known in the art. In embodiments where biotinylated lipids are used in a functionalized NLP, the corresponding target molecules are configured to contain avidin (and/or derivatives thereof), via an additional biotin moiety.

Glutathione-derivatized lipids such as phosphatidylethanolamine-bearing lipid that are suitable in forming NLPs herein described be formed through coupling of glutathione to an appropriate lipid. In embodiments where glutathione-derivatized lipids are used in a functionalized NLP, the corresponding target molecules are configured to contain a glutathione S-transferase fusion protein tag for conjugation. Attachment of a glutathione S-transferase fusion protein tag to the target molecule can be achieved through molecular biological approaches and techniques identifiable by a skilled person.

Strep-tag II-derivatized lipids that are suitable in forming NLPs herein described can be formed through coupling of synthetic strept-tag II to an appropriate lipid, such as phosphatidylethanolamine-bearing lipid, according to techniques identifiable by a skilled person In embodiments where glutathione-derivatized lipids used in a functionalized NLP, the corresponding target molecules are configured to contain a compound such as Strep-Tactin, which is commercially available.

Amine-bearing lipids, such as phosphatidylethanolamine that are suitable in forming NLPs herein described are commercially available or synthesizable by a skilled person using techniques known in the art. In embodiments where amine bearing lipids are used in a functionalized NLP, the corresponding target molecules are configured to contain an amine-reactive moiety, (e.g. active esters, isothiocyanates, sulfonyl chlorides, dichlorotriazines, aryl halides, acyl azides, and the like). Attachment of an amine reactive moiety to the target molecule can be achieved through previously established coupling chemistries and techniques identifiable by a skilled person.

Carboxylic acid-bearing lipids, such as 1,2-dihexadecanoyl-sn-glycero-3-phosphoethanolamine-N-(succinyl) (sodium salt), that are suitable in forming NLPs herein described are commercially available or synthesizable by a skilled person using techniques known in the art. In embodiments where carboxylic acids are used in a functionalized NLP, the corresponding target molecules are configured to contain a reactive primary amines, e.g. lysine side chain presented on the target molecule for binding with the carboxylic acid-bearing lipids.

Thiol-reactive lipids, such as 1,2-dihexadecanoyl-sn-glycero-3-phosphoethanolamine-N-[4-(p-maleimidophenyl) butyramide] (sodium salt), that are suitable in forming NLPs herein described are commercially available or synthesizable by a skilled person using techniques known in the art. In embodiments where thiol-reactive lipids are used in a functionalized NLP, the corresponding target molecules are configured to contain a reduced sulfhydryl moiety, such as reduced cysteine residue.

Free sulfhydryl-bearing lipids, such as 1,2-Dipalmitoyl-sn-Glycero-3-Phosphothioethanol (Sodium Salt), that are suitable in forming NLPs herein described are commercially available or synthesizable by a skilled person using techniques known in the art. In embodiments where free sulfhydryl-bearing lipids are used in a functionalized NLP, the corresponding target molecules are configured to contain thiol-reactive moieties, such as maleimides (and derivatives), haloacetamides, pyridyldithio-propionate, and thiosulfates.

Azide- and alkyne-bearing lipids that are suitable in forming NLPs herein described can be prepared from commercially available components that react with phosphatidylethanolamine-bearing lipids, e.g. 3-(azidotetra(ethyleneoxy)) propionic acid, succinimidyl ester and 3-propargyloxypropanoic acid, succinimidyl ester, respectively. In embodiments where azide- and alkyne-bearing lipids are used in a functionalized NLP, the corresponding target molecules are configured to contain either an acetylene- or azide reactive group, respectively, to form a stable 1,2,3-triazole reaction product.

NLPs comprising the features herein described above can be used as a universal platform for the delivery and presentation of any molecule for several applications. In particular NLPs here described can be used in connection with delivery and presentation of immunogens, i.e. molecules that are capable of eliciting a protective immune response.

The resulting nanoparticle comprises: a scaffold protein, and a functionalized membrane forming lipid attaching an anchor compound substrate assembled in a nanolipoprotein particle. In some embodiments a membrane forming lipid that is not functionalized can also be comprised in the NLP. The immunogenic nanoparticle further comprises a target molecule comprising an immunogen bearing an anchor compound. In the immunogenic particle, the target molecule is attached to the functionalized membrane forming lipid through binding of the anchor compound with the anchor compound substrate. In the immunogenic particle, the target molecule is configured to present the immunogen on the nanolipoprotein particle.

In particular, in certain embodiments, immunogens that can be delivered and presented with the NLP platform, but not limited to, herein described include proteins, polypeptides, toxins, carbohydrates, lipids, fatty acids, and small organic molecules (e.g. dyes, drugs, plasticizers). In particular, immunogens that can be attached to the NLP include proteins that contain large regions or structural domains that are hydrophilic and do not reside within or span a membrane bilayer structure.

The immunogenic NLPs herein describe are configured to present an immunogen on at least one of its surfaces, which is therefore arranged in the NLP to retain its immunogenic reactivity of the molecule as attached. In general, it is know and accepted that immunogenic molecules presented in a dense and patterned motif elicit maximal immune response. Accordingly, in several embodiments immunogenic NLP present multiple copies of an antigen on the NLP, to providing a clustering of the antigen on the NLP.

The terms "antigen" or "immunogen" as used interchangeably herein indicates a substance that prompts the generation of antibodies and/or can cause an immune response. It is generally accepted an antigen is the molecular/structural/chemical motif that binds to an antibody, whereas an immunogen is a substance that initiates or causes an immune response. In the end, all antigens are immunogens but not all immunogens are antigens. Immunogens in the sense of the present disclosure encompass all substances that can be recognized by the immune system. Exemplary immunogens include exogenous immunogens and endogenous immunogens. Exogenous immunogens are immunogens that have entered the body from the outside, for example by inhalation, ingestion, or injection. By endocytosis or phagocytosis, these immunogens are taken into the antigen-presenting cells (APCs) and processed into fragments. APCs then present the fragments to T helper cells ($CD4^+$) by the use of class II histocompatibility molecules on their surface.

Anchor bearing immunogenic molecules can bind or be conjugated specifically to the discoidal surfaces, wherein the latter are comprised, in part, with "functionalized anchor substrates lipids". Successful conjugation or binding can be determined by atomic force microscopy (AFM), surface plasmon resonance (SPR) measurements and other analytical methods/measurements of molecular recognition events.

In some embodiments, immunogenic NiNLPs are prepared as described above except that the functionalized membrane forming lipid (e.g. DOGS-NTA(Ni)) is added so as to comprise between 1% and 100% of overall lipid. This formulation provides NLPs capable of binding His-tagged molecules. In other embodiments, the chelated Ni ion can be replaced with $Cu^{2+}$, $Co^{2+}$, or $Zn^{2+}$ ions and the target protein can be similarly conjugated.

Exemplary immunogenic molecules that can be attached to an NLP herein described include but are not limited to, viral proteins (capsid envelop proteins), outer membrane proteins (OMPs), in general; outer membrane immunogenic carbohydrate moieties; bacterial quorum sensing molecules; other small molecule entities, e.g. plasticizers, dyes and drugs. Reference is made to the exemplary procedures of Examples 4 and 5 illustrating an exemplary immune response of an immunogen presented on a functionalized NLP.

In some embodiments, the formation of immunogenic NLPs herein described is amenable to the incorporation of secondary additives such as compounds directed to enhance immune response e.g. non-human lipoproteins, bacterial peptides, DNA (e.g. CpG motifs), chemokines, cytokines, pattern-recognition receptors (PRR), lipids, polysaccharides, lipopolysaccharides, and the like; in general, agonists and immune stimulatory molecules, synthetic or natural, (known or unknown at this time) can be assembled in or on NLPs, providing for enhanced, specific, rapid immune stimulation at the site of NLP/antigen inoculation and spreading systemically.

In certain embodiments, an adjuvant and an NLP can also be comprised in a system to immunize an individual. In those embodiments, the system comprises: the immunogenic particle herein described and an adjuvant, the immunogenic particle and the adjuvant to be administered to the individual to immunize such individual.

The immunogenic NLPs or the immunogenic composition herein described can also be administered to an individual to immunize the individual. Immunization can be effected by simple intramuscular injection in either the shoulder area or in the gluteus maximus hind muscular region. Particles could be delivered following solubilization in sterile normal saline solution, for example. Such immunizations would be subject to practices and methods approved by the US government Food and Drug Administration (FDA)

In particular, in some embodiments, the immunogenic NLPs can be used as vaccines that can be prepared rapidly and are relatively stable affording the desired protective immune response in accordance with attached immunogen.

The term "vaccine" as used herein indicates a composition, and in particular a biological preparation, that establishes or improves immunity to a particular external pathogenic assault, or an inherent transformational incident resulting in a cancerous condition in mammals. Vaccines in the sense of the present description can be prophylactic, or therapeutic.

With respect to commercial vaccine preparation, the binding of immunogens to immunogenic NLPs is expected to both increase the potency of a vaccine antigen (reducing the need to produce so much immunogen, hence reducing costs), and would be expected to reduce the need for addition of a nonspecific adjuvant making the vaccine safer—since some adjuvants can produce pathogenic immune stimulation and making vaccines less expensive to produce by removing the need for additional adjuvants. Addition of His-tagged immune stimulators on these NiNLPs could provide for safe stimulation of a more rapid and effective immune response (especially in the immunocompromised, young, and the elderly), further enhancing the utility of these vaccines in an emergency situation.

In several embodiments, the immunogenic particles are herein described and related compositions, methods and systems allow cost effective and rapid development of immunogenic compositions that are safe, enable immunization with multivalent/or broad-spectrum response and at the same time, are able to elicit a high levels protection following an adequate stimulation of an host immune response.

In several embodiments, the immunogenic particle, methods and systems herein described allow a rapid and cost effective development of immunogenic compositions against a broad spectrum of immunogenic molecules such as infectious agents, and in particular infectious agents for which a vaccine has not been developed, yet.

Additionally, in several embodiments, the immunogenic particle, methods and systems herein described provide an immunostimulatory particulate delivery/platform system that combined with anchor-bearing immunogenic molecules, such as but not limited to recombinant protein epitopes, provide a new approach to vaccines development.

Furthermore, in several embodiments, the immunogenic particle, methods and systems herein described allow preparation of an immunogenic composition in an amount of time that is considerably reduced compared with corresponding particles and systems of the art.

More particularly, in several embodiments, the immunogenic particle, methods and systems herein described allow rapid preparation of stable vaccine compositions capable of eliciting a desired protective immune response against any attached immunogenic molecule Additionally, in several embodiments, the immunogenic particle, methods and systems herein described can be used as particulate delivery systems, similar in size to certain pathogens while also enabling clustered, oriented and concentrated antigen presentation.

In several embodiments, the immunogenic particle, methods and systems herein described allow incorporation in the immunogenic particles of secondary additives to enhance immune response in the individual.

In some embodiments, the NLPs herein described can be used in connection with delivery of an active target molecule, such as a drug or another molecule of interest that is associated with a desired biological or chemical activity.

In those embodiments, NLPs can be functionalized with at least two active target molecules: a molecular recognition element (MRE) for specific tissue and/or cell targeting and an active target molecule of interest able to provide the biological activity on the specific tissue and/or cell targeted. In those embodiments the NLP acts as the delivery vehicle for the active target molecule of interest, the MRE acts as the targeting moiety that allows the active target molecule of interest to provide the chemical/biological activity on the targeted tissue and/or cells.

The term "MRE" or "Molecular Recognition Element" as used herein, indicates a compound that is capable of specifically binding at least another molecule, through noncovalent bonding such as hydrogen bonding, metal coordination, hydrophobic forces, van der Waals forces, pi-pi interactions, electrostatic, and/or electromagnetic effects. In particular molecular recognition elements include moieties that can directly participate in molecular recognition, and include, but are not limited to, proteins, peptides, nucleic acids, organic molecules, inorganic molecules, carbohydrates, and lipids.

In these embodiments, NLPs will be assembled to contain at least two functionalized membrane forming lipids (e.g.

chelating lipid and thiol active lipid). The MREs and the active target molecule(s) of interest can be functionalized to the NLP surface using the chemical schemes outlined for conjugation of molecules of interest, e.g. His-tagged MRE—chelated lipids and sulfhydroxl/drug-thiol active lipid.

In these embodiments, the relative amount of the two components, MRE and the active target molecule of interest can be controlled through the relative amount of each corresponding anchor-substrate moiety in the NLP bilayer surface. This can be controlled by the input ratios of the membrane-forming and two functionalized anchor-substrate lipids during assembly, as described.

In some embodiments, NLPs are expected to require a small percentage of a reagent such as polyethylene glycol (PEG). PEG allows immunostimulatory particles to evade degradation and uptake by the immune system, and thus will aid in stabilizing the NLP-based drug delivery vehicle. PEGylation of the NLP particle will be achieved using commercially available lipid-PEG molecules (e.g. N-palmitoyl-sphingosine-1-{succinyl[methoxy(polyethylene glycol)750]).

In particular, the active target molecule of interest can comprise a drug compound and the NLPs herein described can be used in connection with delivery of the drug compound alone or together with or other molecules of interest.

In those embodiments, NLPs can be functionalized with at least two target molecules: a molecular recognition element (MRE) for specific tissue and cell targeting (e.g. folic acid to target tumor cell surfaces via the folate receptor) and the active target molecule, for example a therapeutic/pharmaceutical compound (e.g. drugs, proteins, peptides). In this embodiment the NLP acts as the drug delivery vehicle, the MRE acts as the targeting moiety and the drug acts as the therapeutic for treatment of the targeted tissue and/or cells.

In some embodiments, the target molecule of interest can comprise a contrast agent and the NLPs herein described can be used as an image contrast enhancement agent.

In those embodiments, NLPs can be functionalized with two target molecules; a molecular recognition element (MRE) for specific tissue and cell targeting (e.g. folic acid to target tumor cell surfaces) and an image contrast enhancement compound (e.g. gadolinium and/or derivatives thereof). In this embodiment the NLP acts as the image contrast enhancement vehicle, the MRE acts as the targeting moiety and the image contrast enhancement compound is used to enhance the contrast between the tissue of interest (targeted tissue) and surrounding tissue.

In some embodiments, the target molecule of interest can comprise a signal molecule and the NLPs herein described can be used in connection with target detection and biosensors.

In those embodiments, NLPs are functionalized with two target molecules; a molecular recognition element (MRE) for specific tissue, cell, molecular targeting (e.g. folic acid to target tumor cell surfaces) and a signal molecule for detection (e.g. fluorophore). In this embodiment the NLP acts as the vehicle, the MRE acts as the targeting moiety and the detection compound provides the signal necessary for detection.

In those embodiments, a labeled membrane forming lipid can also be used in addition or as a substitute for the detection compound. In this scenario, NLPs will be assembled to contain one functionalized membrane forming lipid (e.g. chelated lipid) for conjugation of MREs and a labeled lipid.

The terms "signal molecule", "label", "labeled molecule" as used herein refer to a molecule capable of detection, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence the wording and "labeling signal" or "detection signal" as used herein indicates the signal emitted from the label that allows detection of the label, including but not limited to radioactivity, fluorescence, chemoluminescence, production of a compound in outcome of an enzymatic reaction and the likes.

In this embodiment, the labeled lipid can be a fluorescently labeled lipid (1-Oleoyl-2-[12-[(7-nitro-2-1,3-benzoxadiazol-4-yl)amino]dodecanoyl]-sn-Glycero-3-Phosphocholine). Further, the detection signal can readily be enhanced and controlled by the total ratio of fluorescently labeled lipid used in the NLP complex (1-100).

In some embodiments, any of the NLP herein described can be comprised in a composition together with a suitable vehicle. The term "vehicle" as used herein indicates any of various media acting usually as solvents, carriers, binders or diluents for an NLP comprised in the composition as an active ingredient.

In some embodiments, where the composition is to be administered to an individual the composition can be a pharmaceutical anti-inflammatory composition, and comprises an NLP and a pharmaceutically acceptable vehicle.

In some embodiments, an NLP can be included in pharmaceutical compositions (e.g. a vaccine) together with an excipient or diluent. In particular, in some embodiments, pharmaceutical compositions are disclosed which contain NLP, in combination with one or more compatible and pharmaceutically acceptable vehicle, and in particular with pharmaceutically acceptable diluents or excipients.

The term "excipient" as used herein indicates an inactive substance used as a carrier for the active ingredients of a medication. Suitable excipients for the pharmaceutical compositions herein disclosed include any substance that enhances the ability of the body of an individual to absorb the NLP. Suitable excipients also include any substance that can be used to bulk up formulations with NLP to allow for convenient and accurate dosage. In addition to their use in the single-dosage quantity, excipients can be used in the manufacturing process to aid in the handling of NLP. Depending on the route of administration, and form of medication, different excipients may be used. Exemplary excipients include but are not limited to antiadherents, binders, coatings disintegrants, fillers, flavors (such as sweeteners) and colors, glidants, lubricants, preservatives, sorbents.

The term "diluent" as used herein indicates a diluting agent which is issued to dilute or carry an active ingredient of a composition. Suitable diluent include any substance that can decrease the viscosity of a medicinal preparation.

In certain embodiments, compositions and, in particular, pharmaceutical compositions can be formulated for systemic administration, which includes parenteral administration and more particularly intravenous, intradermic, and intramuscular administration.

Exemplary compositions for parenteral administration include but are not limited to sterile aqueous solutions, injectable solutions or suspensions including NLP. In some embodiments, a composition for parenteral administration can be prepared at the time of use by dissolving a powdered composition, previously prepared in a freeze-dried lyophilized form, in a biologically compatible aqueous liquid (distilled water, physiological solution or other aqueous solution).

The term "lyophilization" (also known as freeze-drying or cryodesiccation) indicates a dehydration process typically used to preserve a perishable material or make the material more convenient for transport. Freeze-drying works by freezing the material and then reducing the surrounding pressure and adding enough heat to allow the frozen water in the material to sublime directly from the solid phase to gas.

If a freeze-dried substance is sealed to prevent the reabsorption of moisture, the substance may be stored at room temperature without refrigeration, and be protected against spoilage for many years. Preservation is possible because the greatly reduced water content inhibits the action of microorganisms and enzymes that would normally spoil or degrade the substance.

Lyophilization can also causes less damage to the substance than other dehydration methods using higher temperatures. Freeze-drying does not usually cause shrinkage or toughening of the material being dried. In addition, flavours and smells generally remain unchanged, making the process popular for preserving food. However, water is not the only chemical capable of sublimation, and the loss of other volatile compounds such as acetic acid (vinegar) and alcohols can yield undesirable results.

Freeze-dried products can be rehydrated (reconstituted) much more quickly and easily because the process leaves microscopic pores. The pores are created by the ice crystals that sublimate, leaving gaps or pores in their place. This is especially important when it comes to pharmaceutical uses. Lyophilization can also be used to increase the shelf life of some pharmaceuticals for many years.

In pharmaceutical applications freeze-drying is often used to increase the shelf life of products, such as vaccines and other injectables. By removing the water from the material and sealing the material in a vial, the material can be easily stored, shipped, and later reconstituted to its original form for injection According to some embodiments, the functionalized membrane scaffold protein, the scaffold protein, the target molecule and/or any of the NLPs here described can be provided in a system.

In particular, a system for providing a target molecule presenting an anchor compound in a nanoliproprotein particle can comprise the target molecule presenting an anchor compound and a nanolipoprotein particle suitable as a platform for a target molecule, comprising an anchor compound substrate attached to the functionalized membrane forming lipid that is capable to bind the anchor compound presented on the target molecule.

In some embodiments, a system for providing a nanolipoprotein particle suitable as a platform for a target molecule can comprise a scaffold protein and a functionalized membrane forming lipid presenting an anchor compound substrate capable of binding to a corresponding anchor compound presented on the target molecule, and optionally a membrane forming lipid. In the system, the membrane forming lipid, the scaffold protein and the functionalized membrane forming lipid are to be assembled in the nanolipoprotein particle according to methods for providing a nanolipoprotein particle suitable as a platform for a target molecule.

The systems herein disclosed can be provided in the form of kits of parts. For example the target molecule can be included as a molecule alone or in the presence of lipids/detergents for transition in to nano-particles.

In a kit of parts, a functionalized membrane forming lipid, the membrane forming lipid, the target molecule, and/or scaffold protein are comprised in the kit independently possibly included in a composition together with suitable vehicle carrier or auxiliary agents. For example a target molecule can be included in one or more compositions alone and/or included in a suitable vector. Also each of the membrane forming lipid and functionalized membrane forming lipid can be included in a composition together with a suitable vehicle carrier or auxiliary agent. Furthermore, the functionalized membrane forming lipid and the target molecule can be included in various forms suitable for appropriate incorporation into the NLP.

Additional components can also be included and comprise microfluidic chip, reference standards, and additional components identifiable by a skilled person upon reading of the present disclosure.

In the kit of parts herein disclosed, the components of the kit can be provided, with suitable instructions and other necessary reagents, in order to perform the methods here disclosed. In some embodiments, the kit can contain the compositions in separate containers. Instructions, for example written or audio instructions, on paper or electronic support such as tapes or CD-ROMs, for carrying out the assay, can also be included in the kit. The kit can also contain, depending on the particular method used, other packaged reagents and materials (such as wash buffers and the like).

Further details concerning the identification of the suitable carrier agent or auxiliary agent of the compositions, and generally manufacturing and packaging of the kit, can be identified by the person skilled in the art upon reading of the present disclosure.

EXAMPLES

The methods and systems herein disclosed are further illustrated in the following examples, which are provided by way of illustration and are not intended to be limiting.

Example 1

Ni-NLP Assembly

NiNLPs were assembled according to previously reported procedures [Ref. 5] and following the approach schematically illustrated in FIG. 2A.

Briefly, lipids (10% DOGS-NTA-Ni and 90% DMPC) were solubilized in chloroform and aliquoted into glass vials and solvent removed in vacuo. Lipids were then dissolved in TBS buffer (10 mM Tris, 150 mM NaCl) using sodium cholate. A typical NiNLP assembly contained E422K apolipoprotein, lipid, and 20 mM cholate. Samples were incubated at 23.8° C. for at least 1 hour and then dialyzed overnight against TBS. Separation by size exclusion chromatography (SEC) enabled purification of the NiNLPs. Pooled NiNLP containing fractions were concentrated using 50 k MWCO spin filters and analyzed by native gel electrophoresis, i.e. 4-20% Tris-glycine polyacrylamide gels followed by SyproRuby staining and fluorescent imaging. All assemblies were prepared at a 130:1 molar ratio of lipid to E4 22 k.

Example 2

His-Tagged Target Protein Preparation

His-tagged immunogen protein were assembled according to previously reported procedures and following the approach schematically illustrated in FIG. 2B.

In particular, His-tagged proteins were prepared according to the approach illustrated in FIG. 2B, by recombinantly expressing a protein of interest with a His-tag. The His-tagged Env protein from WNV used in the experiments exemplified herein was produced by the use of a proprietary technology, but in principle many types of recombinant technologies identifiable by a skilled person could be used to produce this as well as other target protein of interest.

In particular, DNA expression systems could be utilized for its preparation. The Env used in these studies was synthesized in a eukaryotic cell line (baby hamster kidney—BHK cells) using a patented non-cytopathic Venezuelan equine encephalitic virus replicon (VEErep) expression system [Ref. 1].

To ensure correct folding of Env, it was co-expressed in this VEErep with the WNV prM, since it has been shown that co-expression of these two flavivirus proteins is required for proper Env folding [Ref. 2]. The Env gene was further modified by removal of the nucleic acid sequences encoding the carboxy-terminal membrane binding domains of Env, and replacing these with a synthetic DNA sequence encoding a dual glycine spacer, and six histidine (His) residues. The VEErep containing this construct was also engineered to contain an antibiotic resistance gene (puromycin acetyl transferase). BHK cells transfected with the resulting VEErep were grown in the presence of puromycin (10 ug/ml) to produce BHK cell lines that constitutively expressed the VEErep and secreted the His-tagged truncated Env protein into their culture fluid. This Env protein has been reported to be a useful antigen for detecting antiviral responses to West Nile encephalitis vaccines [Ref. 3], and is used in this report both as the immunogen for NiNLP vaccine generation and as an enzyme-linked immunosorbent assay (ELISA) antigen for detecting vaccine responses to the of Env.

Example 3

NiNLP:His-Tagged Protein Assembly

NiNLPs assembled as exemplified in Example 1 above were conjugated with a target protein including an antigen prepared as exemplified in Example 2, according to the procedure schematically illustrated in FIG. 2C.

In particular, NiNLPs (0.1 ug/uL) were incubated with various concentrations of His-tagged proteins at room temperature for 45 minutes in a volume of 100 uL. A portion from each sample (60 uL) was subsequently filtered using 100 kDa Microcon molecular weight cut-off spin filters and washed three times with 100 uL of buffer. For control experiments, NiNLPs were pre-incubated in buffer containing 4 mM EDTA for 45 minutes at room temperature. For these samples, the wash buffer also contained 4 mM EDTA.

Figure 3:
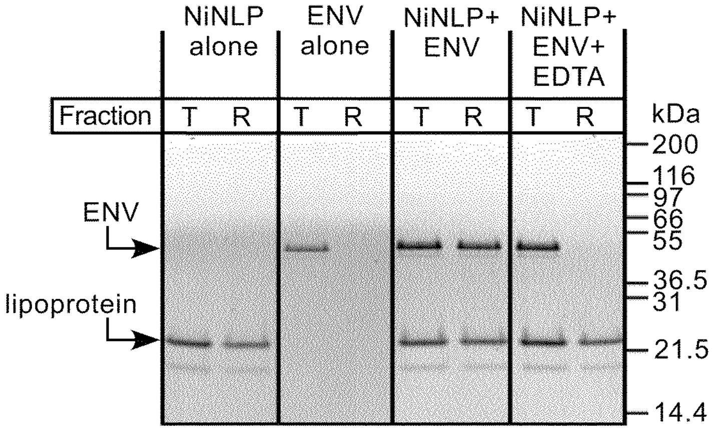
FIG. 3 shows analysis of an NLP platform with anchor-bearing immunogenic protein according to an embodiment herein described: NiNLP:Env constructs. In particular

The results are illustrated in FIG. 3. NiNLP:Env complexes show two bands corresponding to their constituent proteins. When EDTA is added, the complex formation is abrogated as expected following Ni removal by EDTA sequestration.

Figure 4:
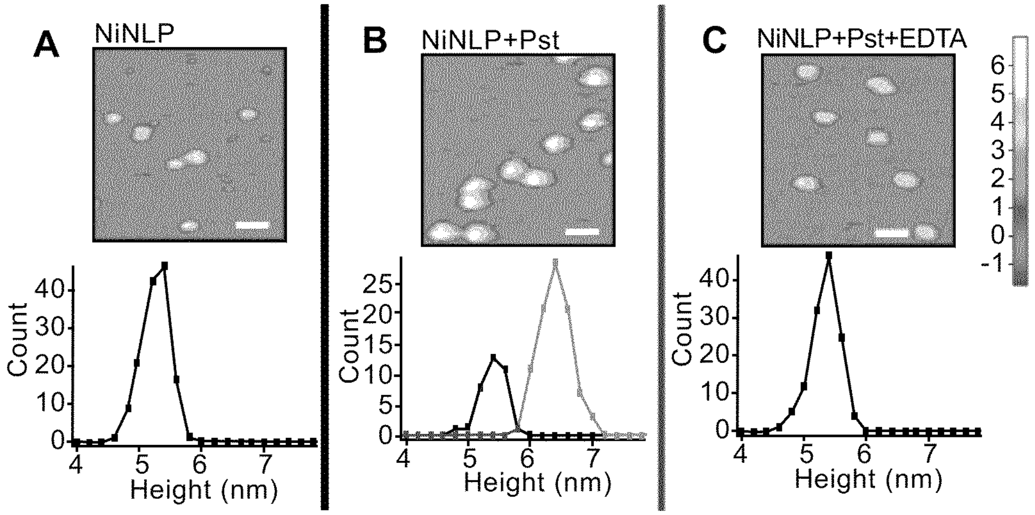
FIG. 4 Atomic force micrographs demonstrating binding of His-tagged protein (pesticin) to NiNLPs.
Figure 5:
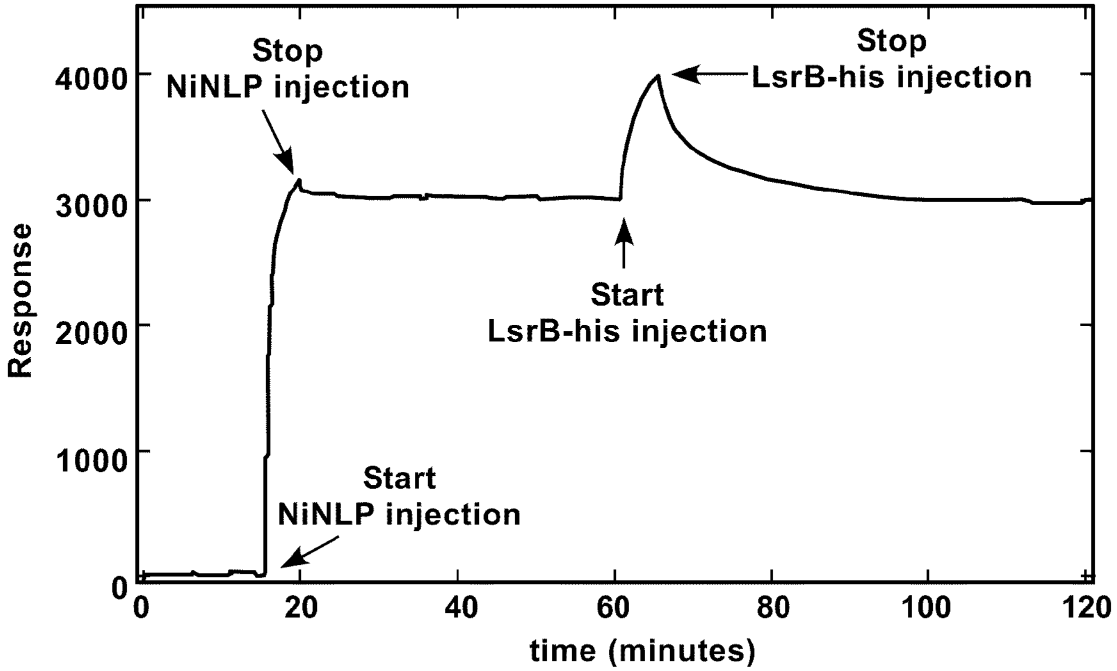
FIG. 5 shows results of conjugation as measured by Surface Plasmon Resonance (SPR). After NiNLP injection, absorption to the lipophilic SPR chip was monitored by change in SPR at the surface. Upon injection of His-tagged LsrB, a *Y. pestis* protein that is part of the ABC transporter complex, a second change in SPR was observed as indicated by the second peak in the SPR profile. After injection of LsrB was stopped, a slow and gradual decrease in the SPR signal was observed, indicative of LsrB disassociation from the NiNLP surface.

This His-tag:Ni interaction exemplified in this Example in connection with Example 1 and 2 was used to conjugate proteins to our NiNLPs, including a bacterial toxin subunit (BoNT), three bacterial cytosolic proteins of various sizes from *Y. pestis*, and the envelope protein (Env) from West Nile virus (WNV), effectively demonstrating the versatility of this conjugation approach. The immobilization of these His-tagged proteins on the NiNLP surface was verified by four independent techniques: size partitioning by centrifugal filtration, size exclusion chromatography (SEC), surface plasmon resonance (SPR) and atomic force microscopy (AFM). FIG. 4 illustrates ability of AFM to monitor the presence of antigens on the NiNLP surface, as demonstrated by the increase in NiNLP height upon incubation with His-tagged antigen. FIG. 5 shows the results of conjugation of his-tagged LsrB as measured by Surface Plasmon Resonance (SPR). After NiNLP injection, absorption to the lipophilic SPR chip was monitored by change in SPR at the surface. Upon injection of his-tagged LsrB, a *Y. pestis* protein that is part of the ABC transporter complex, a second change in SPR was observed as indicated by the second peak in the SPR profile. After injection of LsrB-his was stopped a slow and gradual decrease in the SPR signal was observed, indicative of LsrB-his unbinding.

Figure 2:
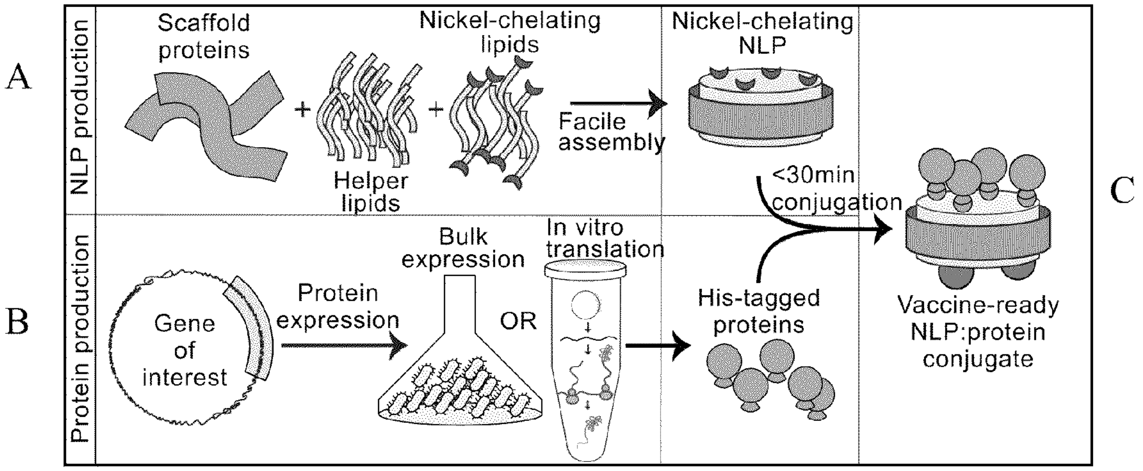
FIG. 2 shows a schematic illustration of a process for assembling immunogenic NLPs according to an embodiment herein described. In particular.

NiNLP production for conjugation to His-tagged proteins performed according the procedure exemplified above and schematically illustrated in FIG. 2, allows performing NiNLP synthesis with control over constituents, size, and functional density. In particular, following the above procedure, conjugation of His-tagged protein to NiNLP can be accomplished in minutes, providing basis for Just-In-Time (JIT) vaccine development.

Example 4

Immune Response Associated with Administration of NiNLP-Immunogen Assemblies To assess the immune response derived from NiNLP:Env constructs, samples were injected into groups of mice, each containing 5 outbred female 6-week-old Swiss Webster mice. NiNLP, Env and diluent (tissue culture media) were injected into their respective groups of mice and served as experimental controls. Collected antisera showed reactivity towards the WNV Env protein in two tests. In the first test, individual sera were diluted 1:100, and tested for their ability to react with WNV E protein in an ELISA assay [Ref. 3].

Figure 6:
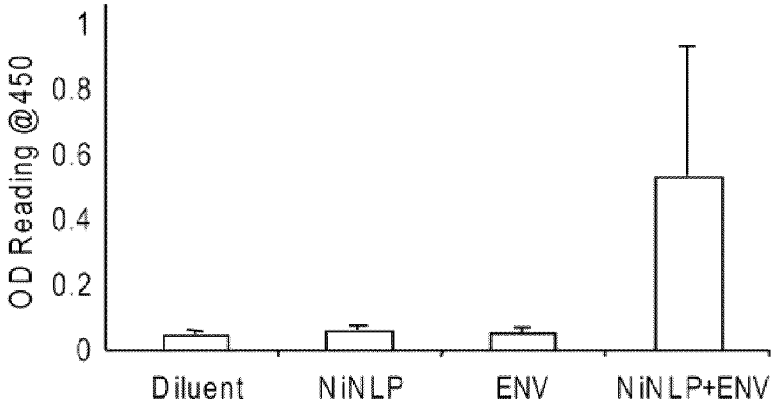
FIG. 6 shows a diagram illustrating the immune response following administration of immunogenic NiNLPs according to an embodiment herein described. In particular, the diagram illustrates ELISA data showing an immune response to the ENV target protein from mice collected 21 days post vaccination performed by intraperitoneal injection to inoculate the mice with immunogenic NiNLPs. ELISAs were performed on 1/100 dilutions of sera from all animals as previously described [Ref. 3]. Bars show the average ELISA OD readings, and extended bars show the standard deviations.

The results illustrated in FIG. 6, demonstrate immunity to Env in all sera collected from mice vaccinated with NiNLP:Env. Sera that were collected from mice vaccinated with NiNLP (alone) or Env (alone) displayed reactivity to Env indistinguishable from mice vaccinated with diluent (FIG. 6).

In a second series of experiments, WNV neutralization tests were performed by mixing pools of the 21-day post-vaccination sera collected from these mice with a WNV virus-like particle surrogate for fully infectious WNV [Ref. 3].

Figure 7:
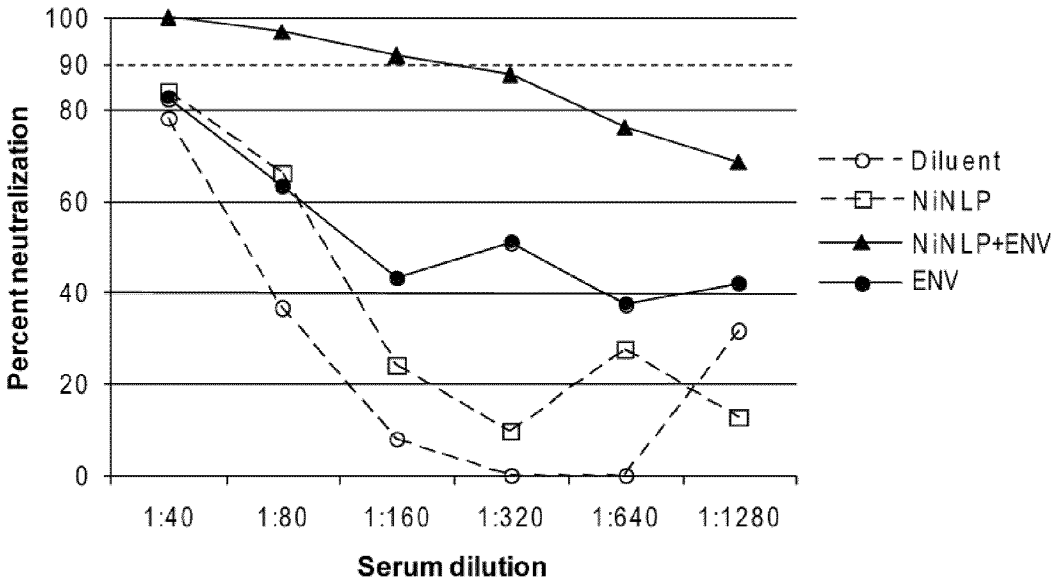
FIG. 7 shows a diagram illustrating neutralization of an immunogen following administration of an immunogenic NiNLP according to an embodiment herein described. In particular, the diagram of FIG. 6 shows neutralization curves illustrating the ability of pooled sera from mice collected 21 days post vaccination to neutralize WNV virus-like particles (VLPs). Assays were performed on dilutions of sera from all animals as previously described [Ref. 3]. Data are expressed as % neutralization relative to VLPs incubated in the absence of any sera.

The results of this test, illustrated in FIG. 7, demonstrate that only the pool of sera from the mice that were vaccinated with NiNLP:Env displayed significant neutralizing activity. Specifically, these sera showed the ability to neutralize 90% of the input VLPs at a sera dilution of 1:160, whereas none of the other sera displayed detectable 90% neutralization at any serum dilution tested (FIG. 7).

When injected into mice, NiNLP:Env constructs gave rise to anti-Env antibody responses significantly better than Env alone, and NiNLP:Env preparation produced a WNV-neutralizing antibody response better than Env alone.

Example 5

Protection from Antigen Challenge Following Administration of NiNLP-antigen Assemblies The ability of NiNLP:Env to protect mice from virulent WNV challenge was performed as previously described [Ref. 3]. Briefly, at 5 weeks post vaccination, the animals treated as exemplified in Example 3 and related FIGS. 6 and 7, were injected by the intraperitoneal (IP) route with 1,000 focus-forming units of WNV, estimated to be approximately 10×50% lethal doses ($LD_{50}$) of virus in 9-week old animals, and observed daily for 21 days. Animals that appeared to be so ill that they would not survive until the next day were euthanized for animal welfare reasons, and recorded as having died the following day.

Figure 8:
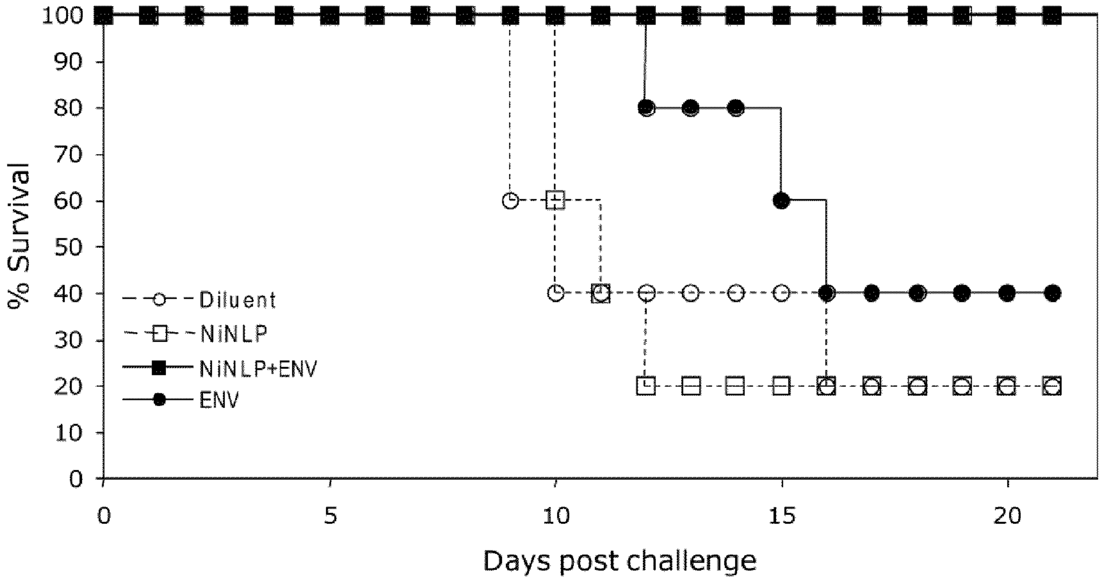
FIG. 8 shows a diagram illustrating protection from viral challenge following administration of immunogenic NiNLPs according to an embodiment herein disclosed. In particular, the diagram of FIG. 7 shows data related to mouse survival over the 21 day period following challenge with virulent WNV.

The data concerning surviving animals were plotted in the chart illustrated in FIG. 8. The survival curve shown in FIG. 8 demonstrated that all mice inoculated with NiNLP:Env survived to 21 days post challenge when the experiment was terminated. The control populations succumbed to infection with the exception of two animals the received Env protein, and one animal in each of the NiNLP (alone) or diluent groups. Application of Fisher's exact test to the 21-day survival data show a significant differences between each of the NiNLP:Env groups and diluent (or NiNLP only) and a significant difference between the combined NLP:Env groups and Env (alone).

When these animals were challenged by intra-peritoneal (IP) administration of live, fully infectious West Nile virus, 100% of the NiNLP:Env-vaccinated animals survived, whereas 60% of the animals vaccinated with Env alone died. At the day of experiment end (day 21) none of the animals remaining showed any signs of illness (lethargy, paralysis, ruffled fur), and all had a weight within 5% of challenge-day weight.

The approach outlined in the present example section is representative of a more general strategy wherein any protein with a His-tag can be used to generate a NLP-based construct in a matter of a few hours and can be administered to afford protective immunity. The approach offers one more advantage; since the NiNLP offers the ability to co-deliver immune stimulators (including, but not limited to: chemokines, cytokines, pattern-recognition receptor (PRR)-agonists, or other immune stimulatory molecules, synthetic or natural, known or unknown at this time) similarly derivatized with a His-tag, providing for enhances, specific, rapid immune stimulation at the site of NiNLP/antigen delivery/uptake. Given the rapidity of preparation, Applicants have coined the term JIT-vaccines; JIT comes from Just-In-Time moniker associated with well practiced manufacturing processes designed to be maximally productive and efficient while maintaining minimal inventory stock.

Applicants have successfully produced numerous NLPs varying in apolipoprotein (scaffold protein) identity and lipid composition. While the goal of NLP development focuses on the incorporation of membrane proteins within the lipid bilayer, the NLPs can also be used as a platform for the conjugation of any His-tagged protein. This is accomplished by introducing low amounts of nickel-chelating lipids during the formation process, resulting in the presentation of chelated nickel to an environment external to the lipid bilayer that is contained by the NLP itself—we refer to these new NLP constructs as NiNLPs. Applicants have used this His-tag:Ni interaction to conjugate proteins to our NiNLPs, including a bacterial toxin subunit (BoNT), three bacterial cytosolic proteins from *Y. pestis*, and the envelope protein (Env) from West Nile virus (WNV), effectively demonstrating the versatility of this conjugation approach. The immobilization of these His-tagged proteins on the NiNLP surface was verified by four independent techniques: size partitioning by centrifugal filtration, size exclusion chromatography (SEC), surface plasmon resonance (SPR) and atomic force microscopy (AFM).

Example 6

Biotinyl-NLP Assembly

Biotinyl-NLPs were assembled in a similar manner to NiNLPs described in Example 1.

Briefly, lipids (2% 18:1 Biotinyl Cap PE and 98% DMPC) were solubilized in chloroform and aliquoted into glass vials and solvent removed in vacuo. Lipids were then dissolved in TBS buffer (10 mM Tris, 150 mM NaCl) using sodium cholate. A typical Biotinyl-NLP assembly contained E422K apolipoprotein, lipid, and 20 mM cholate. Samples were incubated at 23.8° C. for at least 1 hour and then dialyzed overnight against TBS. Separation by size exclusion chromatography (SEC) enabled purification of the Biotinyl-NLPs. Pooled Biotinyl-NLP containing fractions were concentrated using 50 k MWCO spin filters and analyzed by native gel electrophoresis, i.e. 4-20% Tris-glycine polyacrylamide gels followed by SyproRuby staining and fluorescent imaging. Typical assemblies were prepared at a 130:1 molar ratio of lipid to E4 22 k.

Example 7

Biotinyl-NLP:Neutravidin Assembly

Biotinyl-NLPs as exemplified in Example 6 were conjugated with neutravidin.

Figure 9:
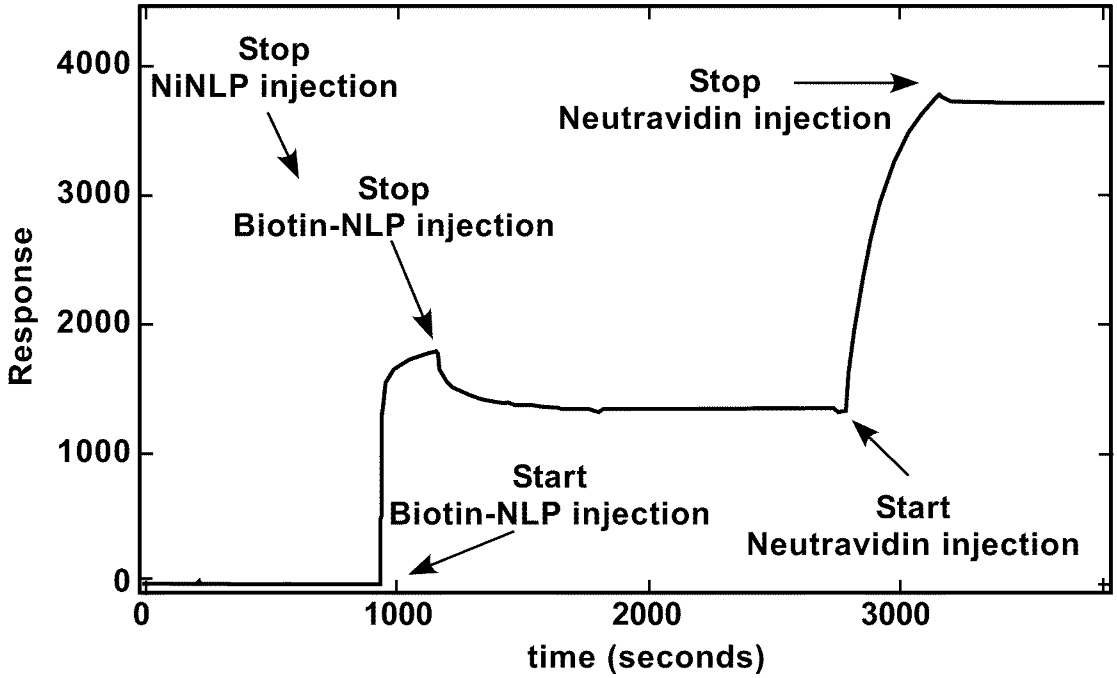
FIG. 9 shows the results of conjugation of neutravidin to Biotinyl-NLPs as measured by SPR. After Biotinyl-NLP injection, absorption to the lipophilic SPR chip was monitored by change in SPR at the surface. Upon injection of neutravidin, a second change in SPR was observed as indicated by the second peak in the SPR profile. After injection of neutravidin was stopped a very slow and gradual decrease in the SPR signal was observed, indicative of neutravidin unbinding.

In particular, Biotinyl-NLPs (2 ug/mL) were immobilized on a Biocore 3000 μl chip. A solution containing 1.35 μM neutravidin was flowed over the immobilized Biotinyl-NLPs. Conjugation of neutravidin to Biotinyl-NLPs was monitored over time, as indicated in FIG. 9. FIG. 9 shows the results of conjugation of Neutravidin to Biotinyl-NLPs as measured by SPR. After Biotinyl-NLP injection, absorption to the lipophilic SPR chip was monitored by change in SPR at the surface. Upon injection of neutravidin, a second change in SPR was observed as indicated by the second peak in the SPR profile. After injection of neutravidin was stopped a very slow and gradual decrease in the SPR signal was observed, indicative of neutravidin unbinding.

Example 8

Example of Maleimide-NLP Assembly

Maleimide-NLPs were assembled in a similar manner to NiNLPs described in Example 1.

Briefly, lipids (10% 1,2-dihexadecanoyl-sn-glycero-3-phosphoethanolamine-N-[4-(p-maleimidophenyl)butyramide] (sodium salt) and 90% DMPC) were solubilized in chloroform and aliquoted into glass vials and solvent removed in vacuo. Lipids were then dissolved in TBS buffer (10 mM Tris, 150 mM NaCl) using sodium cholate. A typical Maleimide-NLP assembly contained E422K apolipoprotein, lipid, and 20 mM cholate. Samples were incubated at 23.8° C. for at least 1 hour and then dialyzed against TBS. Separation by size exclusion chromatography (SEC) enabled purification of the Maleimide-NLPs. Pooled Maleimide-NLP containing fractions were concentrated using 50 k MWCO spin filters and analyzed by native gel electrophoresis, i.e. 4-20% Tris-glycine polyacrylamide gels followed by SyproRuby staining and fluorescent imaging. Typical assemblies were prepared at a 130:1 molar ratio of lipid to E4 22 k.

Example 9

Prophetic Example of Maleimide-NLP:Thiolated Oligonucleotide Conjugation

Maleimide-NLPs as exemplified in Example 8 can be conjugated to thiolated oligonucleotides.

In particular, commercially available thiolated oligonucleotides (e.g. HS-CpG, 22 nucleotides in length with 5' sulfhydryl) are reduced in 5 mM (tris(2-carboxyethyl)phosphine) (TCEP) in TBS buffer (10 mM Tris, 150 mM NaCl). Free TCEP can be removed using a desalting column. The reduced, thiolated oligonucleotide is then incubated with the Maleimide-NLPs at range of molar ratios between 2 and 50 for 2 hours. Conjugation can then be monitored by SEC and/or native gel electrophoresis.

Example 10

Prophetic Example of Azido-NLP Assembly

Azido-NLPs can be assembled in a similar manner to NiNLPs described in Example 1.

Briefly, 2-dimyristoyl-sn-glycero-3-phosphoethanolamine (DMPE) is reacted with 3-(azidotetra(ethyleneoxy)) propionic acid, succinimidyl ester to form an azido-functionalized lipid (Azido-DMPE). Lipids (10% Azido-DMPE and 90% DMPC) are solubilized in chloroform and aliquoted into glass vials and solvent removed in vacuo. Lipids are then dissolved in TBS buffer (10 mM Tris, 150 mM NaCl) using sodium cholate. A typical Azido-NLP assembly will contain E422K apolipoprotein, lipid, and 20 mM cholate. Samples are incubated at 23.8° C. for at least 1 hour and then dialyzed overnight against TBS. Separation by size exclusion chromatography (SEC) enabled purification of the Azido-NLPs. Pooled Azido-NLP containing fractions are concentrated using 50 k MWCO spin filters and analyzed by native gel electrophoresis, i.e. 4-20% Tris-glycine polyacrylamide gels followed by SyproRuby staining and fluorescent imaging. Typical assemblies are prepared at a 130:1 molar ratio of lipid to E4 22 k.

Example 11

Prophetic Example of Azido-NLP: Propargyl-fluorophore Conjugation

Azido-NLPs as exemplified in Example 10 can be conjugated to the commercially-available alkyne-containing fluorophore Alexa Fluor® 488 alkyne (Alexa Fluor® 488 5-carboxamido-(propargyl), bis(triethylammonium salt)).

In particular, commercially-available alkyne-containing fluorophore Alexa Fluor® 488 alkyne (Alexa Fluor® 488 5-carboxamido-(propargyl), bis(triethylammonium salt)) is incubated with the Azido-NLP in TBS buffer (10 mM Tris, 150 mM NaCl) supplemented with ascorbic acid and copper (II) sulfate for 1 hour. Reaction product is purified and monitored by SEC and/or native gel electrophoresis.

Example 12

Prophetic Example of Maleimide/Ni-NLP Assembly

Maleimide/Ni-NLPs can be assembled in a similar manner to NiNLPs described in Example 1.

Briefly, lipids (5% 1,2-dihexadecanoyl-sn-glycero-3-phosphoethanolamine-N-[4-(p-maleimidophenyl)butyramide] (sodium salt), 5% DOGS-NTA-Ni and 90% DMPC) are solubilized in chloroform and aliquoted into glass vials and solvent removed in vacuo. Lipids are then dissolved in TBS buffer (10 mM Tris, 150 mM NaCl) using sodium cholate. A typical Maleimide/NiNLP assembly will contain E422K apolipoprotein, lipid, and 20 mM cholate. Samples are incubated at 23.8° C. for at least 1 hour and then dialyzed against TBS. Separation by size exclusion chromatography (SEC) enables purification of the Maleimide/NiNLPs. Pooled Maleimide/NiNLP containing fractions are concentrated using 50 k MWCO spin filters and analyzed by native gel electrophoresis, i.e. 4-20% Tris-glycine polyacrylamide gels followed by SyproRuby staining and fluorescent imaging. Typical assemblies are prepared at a 130:1 molar ratio of lipid to E4 22 k.

Example 13

Prophetic Example of Maleimide/NiNLP Conjugation to Thiolated Oligonucleotide and His-tagged Protein Maleimide/NiNLPs as exemplified in Example 12 can be conjugated to the commercially-available CpG thiolated oligonucleotide and His-tagged envelope protein from West Nile virus.

In particular, commercially available CpG thiolated oligonucleotides is reduced in 5 mM (tris(2-carboxyethyl)phosphine) (TCEP) in TBS buffer (10 mM Tris, 150 mM NaCl). Free TCEP is then being removed using a desalting column. The reduced, thiolated oligonucleotide is then incubated with the Maleimide/NiNLPs at a molar ratio of 10 for 2 hours. Maleimide/NiNLP:CpG is then purified by SEC. After purification, Maleimide/NiNLP:CpG conjugates are then incubated with His-tagged envelope protein at a molar ratio of 5 for one hour. Conjugation can then be monitored by SEC and/or native gel electrophoresis.

The examples set forth above are provided to give those of ordinary skill in the art a complete disclosure and description of how to make and use the embodiments of the particles, systems and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

The entire disclosure of each document cited (including patents, patent applications, journal articles, abstracts, laboratory manuals, books, or other disclosures) in the Background, Summary, Detailed Description, and Examples is hereby incorporated herein by reference.

It is to be understood that the disclosures are not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

Although any methods and materials similar or equivalent to those described herein can be used in the practice for testing of the specific examples of appropriate materials and methods are described herein.

A number of embodiments of the disclosure have been described. Nevertheless, it will be understood that various modifications may be made without departing from the spirit and scope of the present disclosure. Accordingly, other embodiments are within the scope of the following claims.

REFERENCES

1. Petrakova, O., E. Volkova, R. Gorchakov, S. Paessler, R. M. Kinney, and I. Frolov. 2005. Noncytopathic replication of Venezuelan equine encephalitis virus and eastern equine encephalitis virus replicons in Mammalian cells. J Virol 79:7597-608
2. Konishi, E., and P. W. Mason. 1993. Proper maturation of the Japanese encephalitis virus envelope glycoprotein requires co-synthesis with the premembrane protein. J Virol 67:1672-5.
3. Widman, D. G., T. Ishikawa, R. Fayzulin, N. Bourne, and P. W. Mason. 2008. Construction and characterization of a second-generation pseudoinfectious West Nile virus vaccine propagated using a new cultivation system. Vaccine 26:2762-2771
4. B. A. Chromy, E. Arroyo, C. Blanchette, G. Bench, H. Benner, J. Cappuccio, M. A. Coleman, P. Henderson, A. Hinz, E. A. Kuhn, J. B. Pesavento, B. W. Segelke, T. Sulchek, T. Tarasow, V. L. Walsworth, and P. D. Hoeprich (2007) "Different Apolipoproteins Impact Nanolipoprotein Particle Formation", J. Amer. Chem. Soc. 129:14348-14354
5. Nicholas O. Fischer, Craig D. Blanchette, Brett A. Chromy, Edward A. Kuhn, Brent W. Segelke, Michele Corzett, Graham Bench, Peter W. Mason, and Paul D. Hoeprich (2009) "Immobilization of His-Tagged Proteins on Nickel-Chelating Nanolipoprotein Particles" Bioconjugate Chemistry 20:460-465
6. K. Terpe (2003) "Overview of tag protein fusions: from molecular and biochemical fundamentals to commercial systems" Appl Microbiol Biotechnol, 60:523-533.
7. Hartmuth Kolb and Barry Sharpless (2003) "The growing impact of click chemistry on drug discovery" Drug Discov. Today 8:1128-1137
8. S. R. Simon and W. H. Konigsberg (1966) "Chemical modification of hemoglobins: a study of conformation restraint by internal bridging", Proc Natl Acad Sci USA. 56:749.
9. B. R. Martin and B. F. Cravatt (2009) "Large-scale profiling of protein palmitoylation in mammalian cells " Nat. Methods 6:135-138
10Blanchete CD, Lar R, Benner WH, Pesavento JB, Cappuccio JA, Walsworth V, Sulchek TA. (2008) "Quantifying size distributions of nanolipoprotein particles with single-particle analysis and molecular dynamic simulations" J Lipid Res. 49:1420-30.

What is claimed is:

1. A nanolipoprotein particle suitable as a platform for a target molecule, the nanolipoprotein particle comprising
a scaffold protein, and
a functionalized membrane forming lipid presenting an anchor compound substrate,
wherein the anchor compound substrate is capable of binding a corresponding anchor compound presented on the target molecule.

2. The nanolipoprotein particle of claim 1, wherein the anchor compound substrate is a molecule chelating a bivalent metal ion and the anchor compound is a polyhistidine molecule.

3. The nanolipoprotein particle of claim 2, wherein the bivalent metal ion is selected from the group consisting of $Ni^{2+}$, $Zn^{2+}$, $Co^{2+}$, and $Cu^{2+}$.

4. The nanolipoprotein particle of claim 1, wherein the anchor compound substrate is a negatively charged moiety and the anchor compound is a poly-arginine molecule.

5. The nanolipoprotein particle of claim 1, wherein the anchor compound substrate is a glutathione and the anchor compound is Glutathione S-transferase (GST).

6. The nanolipoprotein particle of claim 1, wherein the anchor compound substrate is biotin and the anchor compound is selected from the group consisting of avidin, streptavidin and neutravidin.

7. The nanolipoprotein particle of claim 1, wherein the anchor substrate compound is a thiol and the anchor compound is selected from the group consisting of maleimide derivatives, haloacetamides, pyridyldithio-propionate and thiosulfates.

8. The nanolipoprotein particle of claim 1, wherein the anchor compound substrate is selected from the group consisting of maleimide derivatives, haloacetamides, pyridyldithio-propionate and thiosulfates, and wherein the anchor compound is a thiol presenting anchor compound.

9. The nanolipoprotein particle of claim 1, wherein the anchor compound substrate is an amine and the anchor compound is selected from the group consisting of active esters, activated carboxylic acids, isothiocyanates, sulfonyl chlorides, dichlorotriazines, aryl halides and acyl azides.

10. The nanolipoprotein particle of claim 1, wherein the anchor compound substrate is selected from the group consisting of active esters, activated carboxylic acids, isothiocyanates, sulfonyl chlorides, dichlorotriazines, aryl halides and acyl azides, and wherein the anchor compound is an amine molecule.

11. The nanolipoprotein particle of claim 1, wherein the anchor compound substrate is an azide molecule and the anchor compound is an acetylene molecule.

12. The nanolipoprotein particle of claim 1, wherein the anchor compound substrate is an acetylene molecule and the anchor compound is an azide molecule.

13. The nanolipoprotein particle of claim 1, wherein the anchor compound substrate is selected from the group consisting of hydrazines, hydroxylamines or aromatic amines and the anchor compound is an aldehyde or ketone molecule.

14. The nanolipoprotein particle of claim 1, wherein the anchor compound substrate is an aldehyde or ketone molecule and the anchor compound is selected from the group consisting of hydrazines, hydroxylamines and aromatic amines.

15. The nanolipoprotein particle of claim 1, wherein the functionalized membrane forming lipid is a biological molecule.

16. The nanolipoprotein particle of claim 1, further comprising a membrane forming lipid.

17. The nanolipoprotein particle of claim 16, wherein the membrane forming lipid is a biological molecule.

18. The nanolipoprotein particle of claim 1, wherein the scaffold protein is an apolipoprotein.

19. The nanolipoprotein particle of claim 1, further comprising the target molecule attached to the functionalized membrane forming lipid, through binding of the anchor compound with the anchor compound substrate.

20. The nanolipoprotein particle of claim 19, wherein the nanolipoprotein particle is configured to present at least one target molecule on a surface of said nanolipoprotein particle.

21. A composition comprising a nanolipoprotein particle according to claim 1 and a suitable vehicle.

22. A nanolipoprotein particle comprising a hydrophilic target molecule, the nanolipoprotein particle comprising:
a scaffold protein
a hydrophilic target molecule attaching an anchor compound, and
a functionalized membrane forming lipid attaching an anchor compound substrate,
wherein the functionalized membrane forming lipid attaches the hydrophilic target molecule through binding of the anchor compound substrate with the anchor compound.

23. A nanolipoprotein particle comprising
multiple target molecules attached to the nanolipoprotein particle formed by assembling a functionalized membrane forming lipid and a scaffold protein,
wherein each of the multiple target molecules attaches an anchor compound, and the functionalized membrane forming lipid attaches an anchor substrate compound, and
wherein the anchor compound binds the anchor substrate compound thus attaching each of the target molecules to the functionalized membrane forming lipid.

24. The nanolipoprotein particle of claim 23, comprising two or more anchor compounds each specifically binding distinct or same target molecules of the multiple target molecules.

25. A nanolipoprotein particle comprising:
an active target molecule attaching a first anchor compound,
a molecular recognition element capable of specifically binding to a predetermined target molecule, the molecular recognition element attaching a second anchor compound
a scaffold protein,
a first functionalized membrane forming lipid attaching a first anchor compound substrate and
a second functionalized membrane forming lipid attaching a second anchor compound substrate;
wherein the active target molecule is attached to the functionalized membrane forming lipid through binding of the first anchor compound with the first anchor compound substrate,
the molecular recognition element is attached to the functionalized membrane forming lipid through binding of the second anchor compound with the second anchor compound substrate, and
wherein the nanolipoprotein is configured to present the active target molecule and the molecular recognition element on said nanolipoprotein particle.

26. The nanolipoprotein particle of claim 24, wherein the first anchor compound substrate specifically binds the first anchor substrate and the second anchor compound specifically binds the second anchor substrate.

27. The nanolipoprotein particle of claim 24, wherein the active target molecule is a drug, a contrast agent or a labeled molecule.

28. A composition comprising a nanolipoprotein particle according to claim 24 and a suitable vehicle.

29. The composition of claim 26, wherein the active target molecule is a drug, the composition is a pharmaceutical composition and the suitable vehicle is a pharmaceutically acceptable vehicle.

30. The composition of claim 26, wherein the active target molecule is a contrast agent, the composition is a pharmaceutical composition and the suitable vehicle is a pharmaceutically acceptable vehicle.

31. A method to delivery an active target molecule to a target cell, the method comprising:
providing a nanolipoprotein particle according to claim 25, the nanolipoprotein particle presenting the active target molecule;
providing the target cell, the target cell presenting a binding molecule capable of specifically binding to the molecular recognition element; and
contacting the nanolipoprotein particle with the target cell to allow specific binding of the molecular recognition element with the binding molecule.

32. An immunogenic particle comprising:
a membrane forming lipid, a scaffold protein, and a functionalized membrane forming lipid attaching an anchor compound substrate assembled in a nanolipoprotein particle; and
a target molecule comprising an immunogen and attaching an anchor compound;
wherein the target molecule is attached to the functionalized membrane forming lipid through binding of the anchor compound with the anchor compound substrate, and
wherein the target molecule is configured to present the immunogen on a surface of the nanolipoprotein particle.

33. An immunogenic composition comprising at least one immunogenic nanolipoprotein particle according to claim 32, together with a suitable adjuvant.

34. A method to immunize an individual, the method comprising administering to the individual at least one of the immunogenic particles of claim 32.

35. A system to immunize an individual, the system comprising:
the immunogenic particle of claim 32 and an adjuvant,
wherein the immunogenic particle and the adjuvant are to be administered to the individual to immunize the individual.

* * * * *